United States Patent
Townsend et al.

(10) Patent No.: US 7,211,115 B2
(45) Date of Patent: *May 1, 2007

(54) PROSTHETIC FOOT WITH TUNABLE PERFORMANCE

(76) Inventors: Barry W. Townsend, 400 Houchin Rd., Bakersfield, CA (US) 93304; Byron Kent Claudino, 9731 Rosedale Hwy., Bakersfield, CA (US) 93312

( * ) Notice: Subject to any disclaimer, the term of this patent is extended or adjusted under 35 U.S.C. 154(b) by 453 days.

This patent is subject to a terminal disclaimer.

(21) Appl. No.: 10/473,680

(22) PCT Filed: Mar. 29, 2002

(86) PCT No.: PCT/US02/09571

§ 371 (c)(1),
(2), (4) Date: Sep. 30, 2003

(87) PCT Pub. No.: WO02/078566

PCT Pub. Date: Oct. 10, 2002

(65) Prior Publication Data

US 2004/0122529 A1    Jun. 24, 2004

Related U.S. Application Data

(63) Continuation-in-part of application No. 09/820,895, filed on Mar. 30, 2001, now Pat. No. 6,562,075.

(51) Int. Cl.
*A61F 2/66* (2006.01)
(52) U.S. Cl. .......................... 623/52; 623/55
(58) Field of Classification Search .............. 623/27, 623/47, 48, 49, 50, 51, 52, 53, 54, 55
See application file for complete search history.

(56) References Cited

U.S. PATENT DOCUMENTS

| 640,540 A | 1/1900 | Daniels |
| 810,180 A | 1/1906 | Wintermute |
| 3,335,428 A | 8/1967 | Gajdos |

(Continued)

FOREIGN PATENT DOCUMENTS

CA    2103341 A1    4/1995

(Continued)

OTHER PUBLICATIONS

PCT Written Opinion from International Application No. PCT/US02/06901.

(Continued)

*Primary Examiner*—David H. Willse
*Assistant Examiner*—Javier G. Blanco
(74) *Attorney, Agent, or Firm*—Antonelli, Terry, Stout & Kraus, LLP.

(57) ABSTRACT

A prosthetic foot (70) incorporates a foot keel (71) and a calf shank (72) connected to the foot keel to form an ankle joint area of the prosthetic foot. The foot keel has forefoot and hindfoot portions and an upwardly arched midfoot portion extending between the forefoot and midfoot portions. The calf shank includes a downward convexly curved lower end which is secured to the foot keel by way of a coupling element (73). The lower end of the calf shank extends upwardly, and initially anteriorly therefrom into a reversely curved portion (75) of the calf shank leading to an upstanding upper end thereof.

20 Claims, 13 Drawing Sheets

U.S. PATENT DOCUMENTS

| | | |
|---|---|---|
| 4,555,817 A | 12/1985 | McKendrick |
| 4,645,509 A | 2/1987 | Poggie et al. |
| 4,721,510 A | 1/1988 | Cooper et al. |
| 4,822,363 A | 4/1989 | Phillips |
| 4,892,554 A | 1/1990 | Robinson |
| 4,911,724 A | 3/1990 | Fikes |
| 4,938,776 A | 7/1990 | Masinter |
| 4,959,073 A | 9/1990 | Merlette |
| 4,994,086 A | 2/1991 | Edwards |
| 5,019,109 A | 5/1991 | Voisin |
| 5,062,859 A | 11/1991 | Naeder |
| 5,066,305 A | 11/1991 | Firth |
| 5,112,356 A | 5/1992 | Harris et al. |
| 5,116,383 A | 5/1992 | Shorter et al. |
| 5,139,525 A | 8/1992 | Kristinsson |
| 5,156,632 A | 10/1992 | Wellershaus |
| 5,181,932 A | 1/1993 | Phillips |
| 5,181,933 A | 1/1993 | Phillips |
| 5,219,365 A | 6/1993 | Sabolich |
| 5,258,039 A | 11/1993 | Goh et al. |
| 5,290,319 A | 3/1994 | Phillips |
| 5,312,669 A | 5/1994 | Bedard |
| 5,314,499 A | 5/1994 | Collier, Jr. |
| 5,376,133 A | 12/1994 | Gramnas |
| 5,376,139 A | 12/1994 | Pitkin |
| 5,376,141 A | 12/1994 | Phillips |
| 5,387,246 A | 2/1995 | Phillips |
| 5,443,522 A | 8/1995 | Hiemisch |
| 5,443,527 A | 8/1995 | Wilson |
| 5,458,656 A | 10/1995 | Phillips |
| 5,482,513 A | 1/1996 | Wilson |
| 5,486,209 A | 1/1996 | Phillips |
| 5,507,838 A | 4/1996 | Chen |
| 5,509,936 A | 4/1996 | Rappoport et al. |
| 5,509,937 A | 4/1996 | Allard et al. |
| 5,509,938 A | 4/1996 | Phillips |
| 5,514,185 A | 5/1996 | Phillips |
| 5,545,230 A | 8/1996 | Kinsinger et al. |
| 5,549,714 A | 8/1996 | Phillips |
| 5,571,213 A | 11/1996 | Allen |
| 5,593,456 A | 1/1997 | Merlette |
| 5,593,457 A | 1/1997 | Phillips |
| 5,653,767 A | 8/1997 | Allen et al. |
| 5,653,768 A | 8/1997 | Kania |
| 5,695,526 A | 12/1997 | Wilson |
| 5,695,527 A | 12/1997 | Allen |
| 5,702,488 A | 12/1997 | Wood et al. |
| 5,725,598 A | 3/1998 | Phillips |
| 5,728,176 A | 3/1998 | Phillips |
| 5,728,177 A | 3/1998 | Phillips |
| 5,746,773 A | 5/1998 | Littig |
| 5,766,264 A | 6/1998 | Lundt |
| 5,776,205 A | 7/1998 | Phillips |
| 5,800,568 A | 9/1998 | Atkinson et al. |
| 5,800,569 A | 9/1998 | Phillips |
| 5,824,112 A | 10/1998 | Phillips |
| 5,897,594 A | 4/1999 | Martin et al. |
| 5,899,944 A | 5/1999 | Phillips |
| 5,944,760 A | 8/1999 | Christensen |
| 5,976,191 A | 11/1999 | Phillips |
| 5,993,488 A | 11/1999 | Phillips |
| 6,051,026 A | 4/2000 | Biedermann et al. |
| 6,071,313 A | 6/2000 | Phillips |
| 6,077,301 A | 6/2000 | Pusch |
| 6,083,265 A | 7/2000 | Shorter et al. |
| 6,099,572 A | 8/2000 | Mosler et al. |
| 6,187,052 B1 | 2/2001 | Molino et al. |
| 6,197,066 B1 | 3/2001 | Gabourie |
| 6,206,932 B1 | 3/2001 | Johnson |
| 6,206,934 B1 | 3/2001 | Phillips |
| 6,228,043 B1 | 5/2001 | Townsend et al. |
| 6,241,776 B1 | 6/2001 | Christensen |
| 6,270,468 B1 | 8/2001 | Townsend et al. |
| 6,280,479 B1 | 8/2001 | Phillips |
| 6,290,730 B1 | 9/2001 | Pitkin et al. |
| 6,350,286 B1 | 2/2002 | Atkinson et al. |
| 6,402,790 B1 | 6/2002 | Celebi |
| 6,406,500 B1 | 6/2002 | Phillips |
| 6,443,995 B1 | 9/2002 | Townsend et al. |
| 6,514,293 B1 | 2/2003 | Jang et al. |
| 6,527,811 B1 | 3/2003 | Phillips |
| 6,562,075 B2 | 5/2003 | Townsend et al. |
| 6,602,295 B1 | 8/2003 | Doddroe et al. |
| 6,663,673 B2 | 12/2003 | Christensen |
| 2002/0040249 A1 | 4/2002 | Phillips |
| 2002/0077706 A1 | 6/2002 | Phillips |
| 2002/0087216 A1* | 7/2002 | Atkinson et al. ............. 623/38 |
| 2002/0116072 A1 | 8/2002 | Rubie et al. |
| 2002/0133237 A1 | 9/2002 | Christesen |
| 2003/0009238 A1 | 1/2003 | Whayne |
| 2003/0028256 A1 | 2/2003 | Townsend et al. |
| 2003/0045944 A1 | 3/2003 | Mosler et al. |
| 2003/0093158 A1 | 5/2003 | Phillips et al. |
| 2003/0120354 A1 | 6/2003 | Doddroe et al. |
| 2003/0191540 A1 | 10/2003 | Townsend et al. |

FOREIGN PATENT DOCUMENTS

| | | |
|---|---|---|
| DE | 325171 C1 | 10/1920 |
| DE | 19717298 C1 | 5/1998 |
| DE | 298 20 904 U1 | 6/1999 |
| DE | 298 23 435 U1 | 9/1999 |
| DE | 29920434 U1 | 5/2000 |
| DK | EP 0 648 479 A1 | 10/1993 |
| EP | 0 331 468 | 9/1989 |
| EP | 0 648 479 A1 | 4/1995 |
| EP | 0793949 A1 | 9/1997 |
| FR | 2 640 499 A1 | 6/1990 |
| FR | 2 734 151 | 11/1996 |
| FR | 2734151 | 11/1996 |
| GB | 2 173 569 | 10/1986 |
| JP | 9-327473 | 12/1997 |
| JP | 11-299815 | 11/1999 |
| WO | WO 91/00070 | 1/1991 |
| WO | WO 94/10942 | 5/1994 |
| WO | WO 97/17042 | 5/1997 |
| WO | WO 00/71061 A1 | 11/2000 |
| WO | WO 02/02034 A1 | 1/2002 |
| WO | WO 02/30340 | 4/2002 |

OTHER PUBLICATIONS

International Search Report from International Application No. PCT/US01/48954.

International Search Report (Apr. 2002); International application no. PCT/US02/09573.

International Search Report (Jul. 1998); International application no. PCT/US02/30471.

International Search Report in corresponding PCT application No. PCT/US02/09571 dated Sep. 27, 2002.

International Search Report in corresponding PCT application No. PCT/US02/09589 dated Sep. 11, 2002.

Perry J. and Shanfield S., *Efficiency of Dynamic Elastic Response Prosthetic Feet; Gait Initiation in Below-Knee Amputees: Analysis of Safe Function; Biomechanical Evaluation of Energy-Storing Prosthetic Feet*, J. Rehabilitation Research and Development Service (Project #A517-RA), 1990, pp. 37, 38 & 44.

Barth, D.G., Schumacher, L. and Thomas, S.S., *Gait Analysis and Energy Cost of Below-Knee Amputees Wearing Six Different Prosthetic Feet*, JPO: Journal of Prosthetics and Orthotics, 1992, vol. 4, No. 2, pp. 626-638.

Menard, M.R. and Murray D.D., *Subjective and Objective Analysis of an Energy-Storing Prosthetic Foot*, Journal of Prosthetics and Orthotics, 1989, vol. 1, No. 4, pp. 173-183.

Menard, M.R., McBride, M.E., Sanderson, D.J. and Murray, D.D., *Comparative Biomechanical Analysis of Energy-Storing Prosthetic Feet*, Archives of Physical Medicine and Rehabilitation, May 1992, vol. 73, pp. 451-458.

Prince, F., Winter, D.A. et al., *Mechanical Efficiency During Gait of Adults with Transtibial Amputation: A Pilot Study Comparing the SACH, Seattle, and Golden-Ankle Prosthetic Feet*, Journal of Rehabilitation Research and Development, Jun. 1998, vol. 35, No. 2, pp. 177-185.

Winter, D.A., *Biomechanics of Human Movement*, John Wiley & Sons, Inc., 1979, pp. 61, 117-121.

Mann, R.A. and Hagy, J.L., *The Function of the Toes in Walking, Jogging and Running*, J.J.B. Lippincott Company, 1979, vol. 142, pp. 24-29.

Perry, J., *Gait Analysis: Normal and Pathological Function*, SLACK Incorporated, Thorofare, NJ, 1992, Chapter 4: *Ankle Foot Complex*, Chapter 19: *Ground Reaction Force and Vector Analysis*, Chapter 21: *Energy Expenditure*.

Valmassy, R.L., *Clinical Biomechanics of the Lower Extremities*, Mosby, 1996, Chapter 1: *Lower Extremity Function and Normal Mechanics*.

Hsu, M. and Nielsen, D., et al., *Physiological Measurements of Walking and Running in People with Transtibial Amputations With 3 Different Prostheses*, Journal of Othopaedic & Sports Physical Therapy, Sep. 1999; vol. 29, No. 9, pp. 527-533.

Macfarlane, P.A. and Nielsen, D.H. et al., *Gait Comparisons for Below-Knee Amputees Using a Flex-Foot™ Versus a Conventional Prosthetic Foot*, Journal of Prosthetic and Orthotics, 1991, vol. 3, No. 4, pp. 526-537.

Neilson, D.H. and Shurr, D.G. et al., *Comparison of Energy Cost and Gait Efficiency During Ambulation in Below-Knee Amputees Using Different Prosthetic Feet—A Preliminary Report*, Journal of Prosthetics and Orthotics, 1988, vol. 1, No. 1, pp. 24-31.

Macfarlane, P.A. and Nielsen, D.H. et al., *Perception of Walking Difficulty by Below-Knee Amputees Using a Conventional Foot Versus the Flex-Foot*, Journal of Prosthetics and Orthotics, 1991, vol. 3, No. 3., pp. 503-508.

Childress, D., *Mechanical Properties of Prosthetic and Human Feet: From Shoes to Computer Alignment*, 2nd Conference of Advanced Prosthetics, Apr. 2002.

Wirta, R.W. et al., *Effect on Gait Using Various Prosthetic Ankle-Foot Devices*, Journal of Rehabilitation Research and Development, 1991, vol. 28, No. 2, pp. 13-24.

Winter, D.A. and Patia A.E. et al., *Biomechanical Walking Pattern Changes in the Fit and Healthy Elderly*, Physical Therapy, Jun. 1990, vol. 70, No. 6, pp. 340/15-346/21.

Ayyappa, E., *Normal Human Locomotion, Part 1: Basic Concepts and Terminology*, Journal of Prosthetics and Orthotics, Winter 1997, vol. 9, No. 1, pp. 10-17.

Ayyappa, E., *Normal Human Locomotion, Part 2: Motion, Ground-Reaction Force and Muscle Activity*, Journal of Prosthetics and Orthotics, Spring 1997, vol. 9, No. 2, pp. 49-57.

Winter, D.A., *Biomechanics and Motor Control of Humans Movement*, University of Waterloo, John Wiley & Sons, Inc., 1990, Chapter 7.

J.B. Saunders, et al., *The Major Determinants in Normal and Pathological Gait*, Journal of Bone and Joint Survey, Jul. 1953, vol. 35A, No. 3, pp. 543-558.

Komi, P.V., *Stength and Power In Sport*, Blackwell Scientific Publications, 1992, Chapter 6B, pp. 115-129.

McComas, A.J., *Skeletal Muscle Form and Function*, Human Kinetics, Champaign, IL, 1996, pp. 326-375.

Mattes, S.J., et al., *Walking Symmetry and Energy Cost in Persons with Unilateral Transtibial Amputations: Matching Prosthetic and Intact Limb Inertial Properties*, Archives of Physical Medicine and Rehabilitation, May 2000, vol. 81, pp. 561-568.

Bojsen-Moller, F., *Calcaneocuboid Joint and Stability of the Longitudinal Arch of the Foot at High and Low Gear Push Off*, Journal of Anatomy, Aug.-Dec. 1979, vol. 129, pp. 165-176.

Hicks, J.H., *The Mechanics of the Foot, The Plantar Aponeurosis and the Arch*, Journal of Anatomy, 1954, vol. 88, Pt. 1, pp. 25-31.

Bunnstrom, S. (revised by R. Dickinson), *Clinical Kinesiology*, F.A. Davis Company, Philadelphia, 1972, p. 35.

Stiehl, J. *Inman's Joints of the Ankle* (2nd Ed.), Williams & Wilkins, Baltimore, MD, 1991, p. 39.

Bateni, H., et al., *Kinematic and Kinetic Variations of Below-Knee Amputee Gait*, Prosthetic and Orthotic Science, 2002, vol. 14, No. 1, pp. 2-10.

International Search Report; PCT/US03/09506; filed Mar. 31, 2003.

Universal Offset Pyramid Adapters ; 2 pages.

International Search Report; PCT/US05/11304 ; Filing Date : Apr. 1, 2005.

International Search Report; PCT/US05/11291; Filing Date: Apr. 1, 2005.

Supplementary Partial European Search Report; EP 02 75 7836; Date : Mar. 7, 2006.

Supplementary Partial European Search Report; EP 02 71 3785; Date : Mar. 7, 2006.

International Search Report; PCT/US05/34037; Filing Date: Sep. 26, 2005.

Supplementary European Search Report; EP 02 71 3785; May 22, 2006.

Supplementary European Search Report; EP 02 75 7836; May 25, 2006.

* cited by examiner

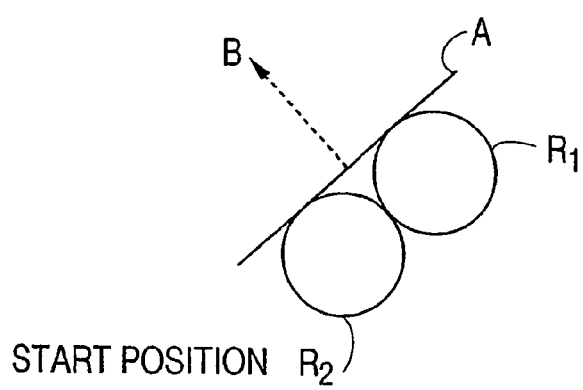
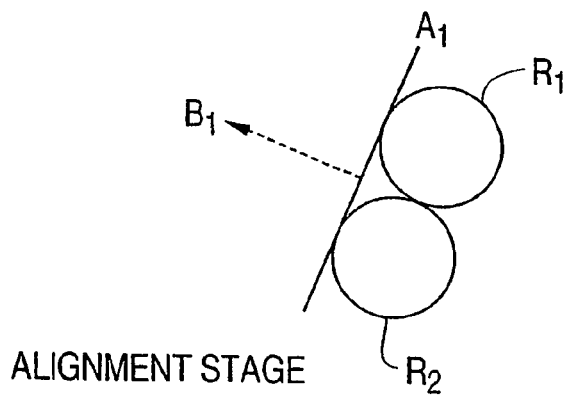
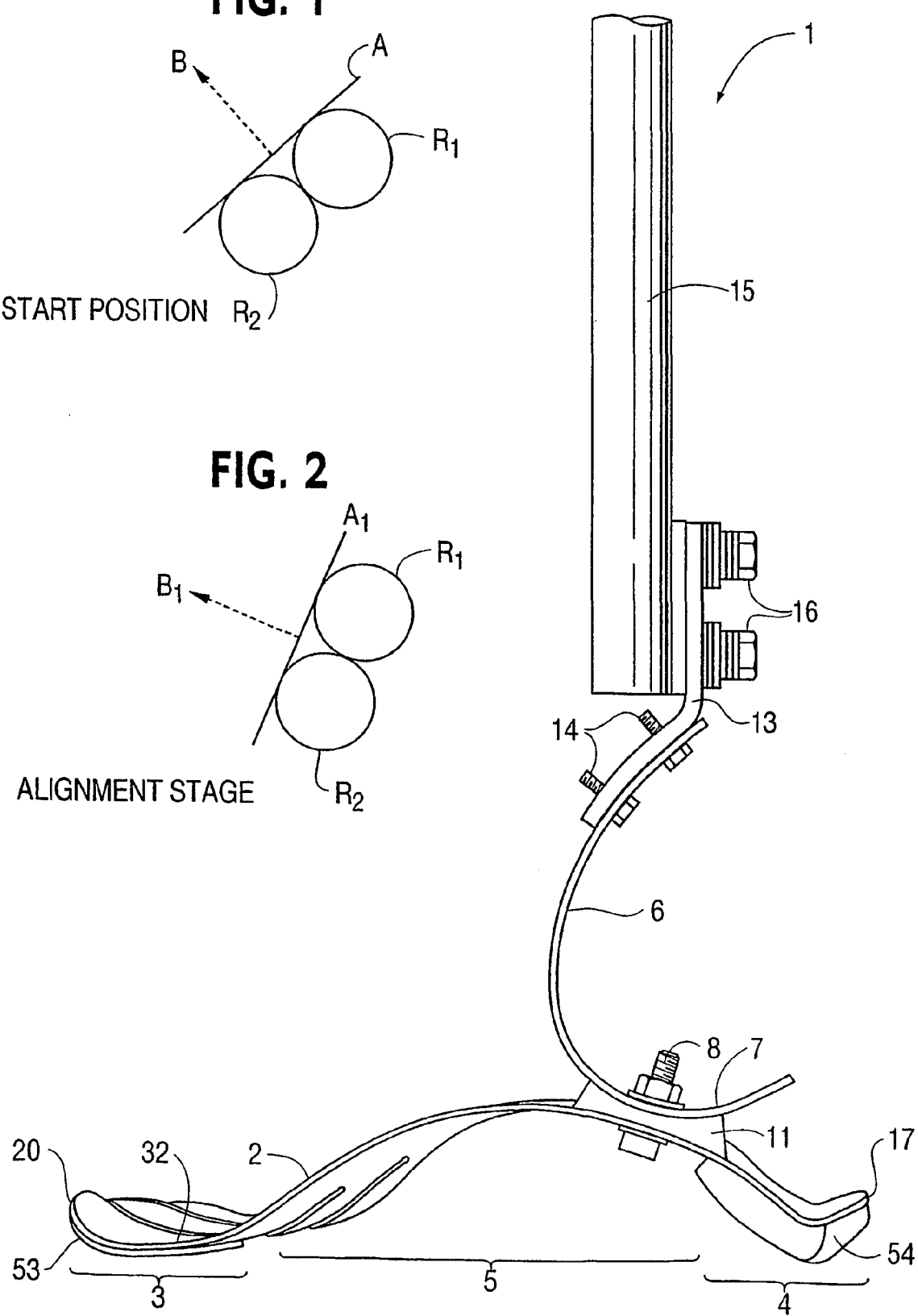

46

47

48

49

50

51

PROSTHETIC FOOT WITH TUNABLE PERFORMANCE

RELATED APPLICATIONS

This application is a U.S. national stage application filed under 35 U.S.C. §371 of international application PCT/US02/09571 and a continuation in part of U.S. application Ser. No. 09/820,895, filed Mar. 30, 2001, now U.S. Pat. No. 6,562,075 issued May 13, 2003, the priority of which is claimed.

TECHNICAL FIELD

The present invention relates to a high performance prosthetic foot providing improved dynamic response capabilities as these capabilities relate to applied force mechanics.

BACKGROUND ART

A jointless artificial foot for a leg prosthesis is disclosed by Martin et al. in U.S. Pat. No. 5,897,594. Unlike earlier solutions wherein the artificial foot has a rigid construction provided with a joint in order to imitate the function of the ankle, the jointless artificial foot of Martin et al. employs a resilient foot insert which is arranged inside a foot molding. The insert is of approximately C-shaped design in longitudinal section, with the opening to the rear, and takes up the prosthesis load with its upper C-limb and via its lower C-limb transmits that load to a leaf spring connected thereto. The leaf spring as seen from the underside is of convex design and extends approximately parallel to the sole region, forward beyond the foot insert into the foot-tip region. The Martin et al. invention is based on the object of improving the jointless artificial foot with regard to damping the impact of the heel, the elasticity, the heel-to-toe walking and the lateral stability, in order thus to permit the wearer to walk in a natural manner, the intention being to allow the wearer both to walk normally and also to carry out physical exercise and to play sports. However, the dynamic response characteristics of this known artificial foot are limited. There is a need for a higher performance prosthetic foot having improved applied mechanics design features which can improve amputee athletic performances involving activities such as running, jumping, sprinting, starting, stopping and cutting, for example.

Other prosthetic feet have been proposed by Van L. Phillips which allegedly provide an amputee with an agility and mobility to engage in a wide variety of activities which were precluded in the past because of the structural limitations and corresponding performances of prior art prostheses. Running, jumping and other activities are allegedly sustained by these known feet which, reportedly, may be utilized in the same manner as the normal foot of the wearer. See U.S. Pat. Nos. 6,071,313; 5,993,488; 5,899,944; 5,800,569; 5,800,568; 5,728,177; 5,728,176; 5,824,112; 5,593,457 5,514,185; 5,181,932; and 4,822,363, for example.

DISCLOSURE OF INVENTION

In order to allow the amputee athlete to attain a higher level of performance, there is a need for a high performance prosthetic foot having improved applied mechanics, which foot can out perform the human foot and also out perform the prior art prosthetic feet. It is of interest to the amputee athlete to have a high performance prosthetic foot having improved applied mechanics, high low dynamic response, and alignment adjustability that can be fine tuned to improve the horizontal and vertical components of activities which can be task specific in nature.

The prosthetic foot of the present invention addresses these needs. According to an example embodiment disclosed herein, the prosthetic foot of the invention comprises a longitudinally extending foot keel having a forefoot portion at one end, a hindfoot portion at an opposite end and a relatively long midfoot portion extending between and upwardly arched from the forefoot and hindfoot portions. A calf shank including a downward convexly curved lower end is also provided. An adjustable fastening arrangement attaches the curved lower end of the calf shank to the upwardly arched midfoot portion of the foot keel to form an ankle joint area of the prosthetic foot.

The adjustable fastening arrangement permits adjustment of the alignment of the calf shank and the foot keel with respect to one another in the longitudinal direction of the foot keel for tuning the performance of the prosthetic foot. By adjusting the alignment of the opposed upwardly arched midfoot portion of the foot keel and the downward convexly curved lower end of the calf shank with respect to one another in the longitudinal direction of the foot keel, the dynamic response characteristics and motion outcomes of the foot are changed to be task specific in relation to the needed/desired horizontal and vertical linear velocities. A multi-use prosthetic foot is disclosed having high and low dynamic response capabilities, as well as biplanar motion characteristics, which improve the functional outcomes of amputees participating in sporting and/or recreational activities. A prosthetic foot especially for sprinting is also disclosed.

The calf shank can have its lower end downward, convexly curved and extending upwardly, and initially anteriorly into a reversely curved portion of the calf shank leading to an upstanding upper end thereof. With this construction, a cosmetic covering in the shape of a human foot and lower leg easily located over the foot keel and at least the lower end of the calf shank with the calf shank rising upwardly from the foot keel within the lower leg covering. A plurality of longitudinally extending grooves and fins formed on the posteriorly facing surface of the reversely curved portion facilitate resilient compression of the calf shank while resisting expansion thereof in response to forces on the calf shank during use of the prosthetic foot.

These and other objects, features and advantages of the present invention become more apparent from a consideration of the following detailed description of disclosed example embodiments of the invention and the accompanying drawings.

BRIEF DESCRIPTION OF THE DRAWINGS

FIG. 1 is a schematic illustration representing the two adjacent radii of curvatures $R_1$ and $R_2$, one against the other, of a foot keel and calf shank of a prosthetic foot of the invention which creates a dynamic response capability and motion outcome of the foot in gait in the direction of arrow B which is perpendicular to the tangential line A connecting the two radii.

FIG. 2 is a view similar to FIG. 1 but showing the alignment of the two radii having been changed in the prosthetic foot according to the invention to increase the horizontal component and decrease the vertical component of the dynamic response capability and motion outcome of the foot in gait so that arrow $B_1$, perpendicular to tangential line $A_1$, is more horizontally directed than is the case depicted in FIG. 1.

FIG. 3 is a side view of a prosthetic foot according to an example embodiment of the invention with pylon adapter and pylon connected thereto for securing the foot to the lower leg of an amputee.

BEST MODE FOR CARRYING OUT THE INVENTION

Figure 4:
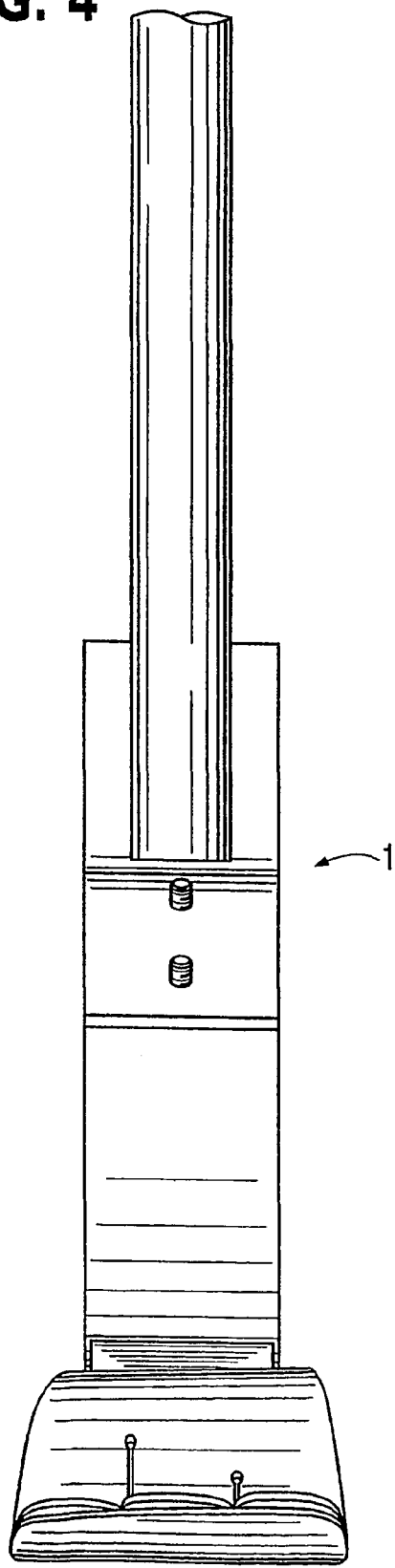
FIG. 4 is a front view of the prosthetic foot with pylon adapter and pylon of FIG. 3.
Figure 5:
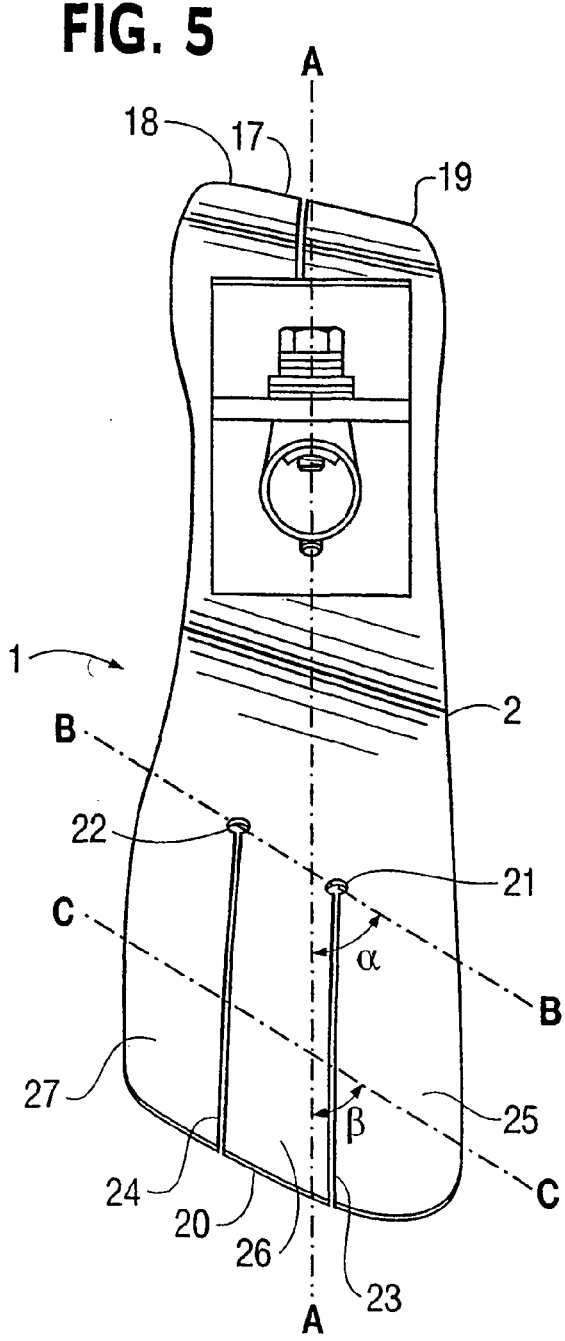
FIG. 5 is a top view of the embodiment of FIGS. 3 and 4.

Referring now to the drawings, a prosthetic foot 1 in the example embodiment of FIGS. 3–5 is seen to comprise a longitudinally extending foot keel 2 having a forefoot portion 3 at one end, a hindfoot portion 4 at an opposite end and a relatively long midfoot portion 5 extending between and upwardly arched from the forefoot and hindfoot portions. The midfoot portion 5 is upward convexly curved over its entire longitudinal extent between the forefoot and hindfoot portions in the example embodiment.

An upstanding calf shank 6 of the foot 1 is attached at a portion of a downward convexly curved lower end 7 thereof to a proximate, posterior surface of the keel midfoot portion 5 by way of a releasable fastener 8 and coupling element 11. The fastener 8 is a single bolt with nut and washers in the example embodiment, but could be a releasable clamp or other fastener for securely positioning and retaining the calf shank on the foot keel when the fastener is tightened.

Figure 8:
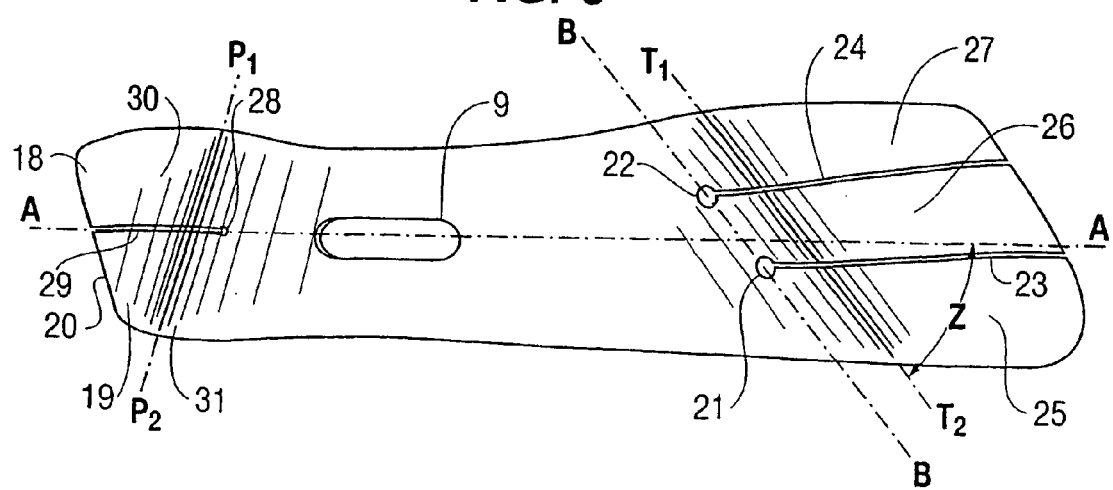
FIG. 8 is a bottom view of the foot keel in the prosthetic foot in FIG. 3 which. provides high low dynamic response characteristics as well as biplanar motion capabilities.
Figure 15:
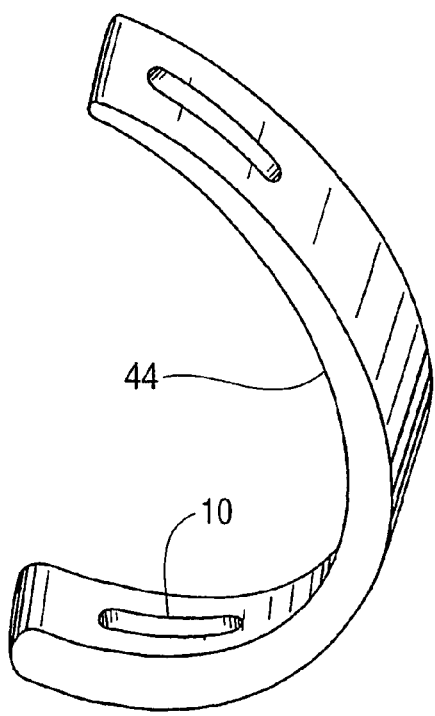
FIG. 15 is a side view from slightly above and to the front of a parabola shaped calf shank of the prosthetic foot of the invention, the thickness of the calf shank tapering toward its upper end.

A longitudinally extending opening 9 is formed in a proximate, posterior surface of the keel midfoot portion 5, see FIG. 8. A longitudinally extending opening 10 is also formed in the curved lower end 7 of the calf shank 6 like that shown in FIG. 15, for example. The releasable fastener 8 extends through the openings 9 and 10 to permit adjusting the alignment of the calf shank and the foot keel with respect to one another in the longitudinal direction, A—A in FIG. 5, when the fastener 8 is loosened or released for tuning the performance of the prosthetic foot to be task specific. Thus, the fastener 8, coupling element 11 and longitudinally extending openings 9 and 10 constitute an adjustable fastening arrangement for attaching the calf shank to the foot keel to form an ankle joint area of the prosthetic foot.

The effect of adjusting the alignment of the calf shank 6 and foot keel 2 are seen from a consideration of FIGS. 1 and 2, wherein the two radii $R_1$ and $R_2$, one next to another, represent the adjacent, facing, domed or convexly curved surfaces of the foot keel midportion 5 and the calf shank 6. When two such radii are considered one next to another, motion capability exists perpendicular to a tangential line, A in FIG. 1, $A_1$ in FIG. 2, drawn between the two radii. The interrelationship between these two radii determines a direction of motion outcomes. As a consequence, dynamic response force application of the foot 1 is dependent on this relationship. The larger the radius of a concavity, the more dynamic response capability. However, the tighter a radius, the quicker it responds.

The alignment capability of the calf shank and foot keel in the prosthetic foot of the invention allows the radii to be shifted so that horizontal or vertical linear velocities with the foot in athletic activities are affected. For example, to improve the horizontal linear velocity capability of the prosthetic foot 1, an alignment change can be made to affect the relationship of the calf shank's radius and the foot keel radius. That is, to improve the horizontal linear velocity characteristic, the bottom radius $R_2$, of the foot keel, is made more distal than its start position, FIG. 2 as compared with FIG. 1. This changes the dynamic response characteristics and motion outcomes of the foot 1 to be more horizontally directed and as a result greater horizontal linear velocity can be achieved with the same applied forces.

Figure 23:
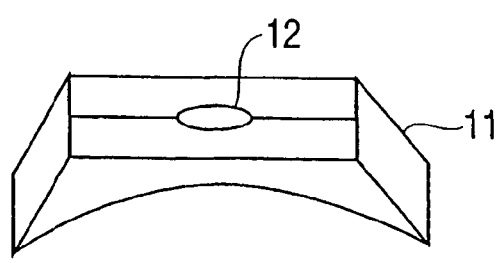
FIG. 23 is a side view, from slightly above, of an aluminum or plastic coupling element used in the adjustable fastening arrangement of the invention for attaching the calf shank to the foot keel as shown in FIG. 3.
Figure 24:
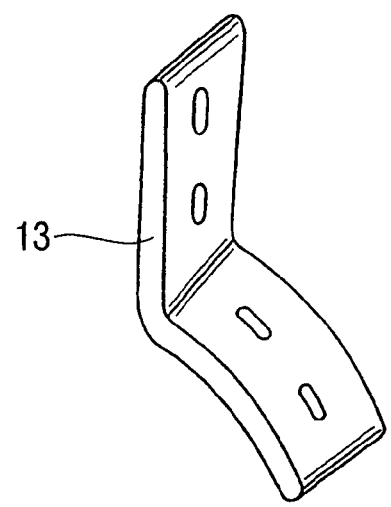
FIG. 24 is a view from the side and slightly to the front of a pylon adapter used on the prosthetic foot of FIGS. 3–5 for connecting the foot to a pylon to be attached to an amputee's leg.

The amputee can, through practice, find a setting for each activity that meets his/her needs as these needs relate to horizontal and vertical linear velocities. A jumper and a basketball player, for example, need more vertical lift than a sprint runner. The coupling element 11 is a plastic or metal alloy, such as aluminum, alignment coupling (see FIGS. 3, 4 and 23) sandwiched between the attached foot keel 2 and calf shank 6. The releasable fastener 8 extends through a hole 12 in the coupling element. The coupling element extends along the attached portion of the calf shank and the proximate, posterior surface of the keel midfoot portion 5.

The curved lower end 7 of the calf shank 6 is in the shape of a parabola with the smallest radius of curvature of the parabola located at the lower end and extending upwardly, and initially anteriorly in the parabola shape. A posteriorly facing concavity is formed by the curvature of the calf shank as depicted in FIG. 3. The parabola shape is advantageous in that it has increased dynamic response characteristics in creating both improved horizontal linear velocity associated with the relatively larger radii proximal terminal end thereof, while having a smaller radius of curvature at its lower end for quicker response characteristics. The larger radii of curvature at the upper end of the parabola shape enable the tangential line A, explained with reference to FIGS. 1 and 2, to remain more vertically oriented with changes in alignment, which creates improved horizontal linear velocity.

A pylon adapter 13 is connected to the upper end of the calf shank 6 by fasteners 14. The adapter 13 in turn is secured to the lower end of pylon 15 by fasteners 16. Pylon 15 is secured to the lower limb of the amputee by a supporting structure (not shown) attached to the leg stump.

The forefoot, midfoot and hindfoot portions of the foot keel 2 are formed of a single piece of resilient material in the example embodiment. For example, a solid piece of material, plastic in nature, having shape-retaining characteristics when deflected by the ground reaction forces can be employed. In particular, a high strength graphite, laminated with epoxy thermosetting resins, or extruded plastic utilized under the tradename of Delran, or degassed polyurethane copolymers, may be used to form the foot keel and also the calf shank. The functional qualities associated with these materials afford high strength with low weight and minimal creep. The thermosetting epoxy resins are laminated under vacuum utilizing prosthetic industry standards. The polyurethane copolymers can be poured into negative molds and the extruded plastic can be machined. Each material of use has its advantages and disadvantages.

The resilient material's physical properties as they relate to stiffness, flexibility and strength are all determined by the thickness of the material. A thinner material will deflect easier than a thicker material of the same density. The material utilized, as well as the physical properties, are associated with the stiffness to flexibility characteristics in the prosthetic keel and calf shank. The thickness of the keel and calf shank are uniform or symmetrical in the example embodiment of FIGS. 3–5, but the thickness along the length of these components can be varied as discussed below, such as by making the hindfoot and forefoot areas thinner and more responsive to deflection in the midfoot region.

To aid in providing the prosthetic foot 1 with a high low dynamic response capability, the midfoot portion 5 is formed by a longitudinal arch such that the medial aspect of the longitudinal arch has a relatively higher dynamic response capability than the lateral aspect of the longitudinal arch. For this purpose, in the example embodiment, the medial aspect of the longitudinal arch concavity is larger in radius than the lateral aspect thereof. The posterior end 17 of the hindfoot portion 4 is shaped in an upwardly curved arch that reacts to ground reaction forces during heel strike by compressing for shock absorption. The heel formed by the hindfoot portion 4 is formed with a posterior lateral corner 18 which is more posterior and lateral than the medial corner 19 to encourage hindfoot eversion during initial contact phase of gait. The anterior end 20 of the forefoot portion 3 is shaped in an upwardly curved arch to simulate the human toes being dorsiflexed in the heel rise toe off position of the late stance phase of gait. Rubber or foam pads 53 and 54 are provided on the lower forefoot and hindfoot as cushions.

Improved biplanar motion capability of the prosthetic foot is created by medial and lateral expansion joint holes 21 and 22 extending through the forefoot portion 3 between dorsal and plantar surfaces thereof. Expansion joints 23 and 24 extend forward from respect ones of the holes to the anterior edge of the forefoot portion to form medial, middle and lateral expansion struts 25–27 which create improved biplanar motion capability of the forefoot portion of the foot keel. The expansion joint holes 21 and 22 are located along a line, B—B in FIG. 5, in the transverse plane which extends at an angle a of 350 to the longitudinal axis A—A of the foot keel with the medial expansion joint hole 21 more anterior than the lateral expansion joint hole 22. The expansion joint holes 21 and 22 as projected on a sagittal plane are inclined at an angle of 450 to the transverse plane with the dorsal aspect of the holes being more anterior than the plantar aspect. With this arrangement, the distance from the releasable fastener 8 to the lateral expansion joint hole 22 is shorter than the distance from the releasable fastener to the medial expansion joint hole 21 such that the lateral portion of the prosthetic foot 1 has a shorter toe lever than the medial for enabling midfoot high and low dynamic response.

The anterior of the hindfoot portion 4 of the foot keel 2 further includes an expansion joint hole 28 extending through the hindfoot portion 4 between dorsal and plantar surfaces thereof. An expansion joint 29 extends posteriorly from the hole 28 to the posterior edge of the hindfoot portion to form expansion struts 30 and 31. These create improved biplanar motion capability of the hindfoot portion of the foot.

A dorsal aspect of the midfoot portion 5 and the forefoot portion 3 of the foot keel 2 form the upwardly facing concavity, 32 in FIG. 3, so that it mimics in function the fifth ray axis of motion of a human foot. That is, the concavity 32 has a longitudinal axis C—C which is oriented at an angle 13 of 15° to 35° to the longitudinal axis A—A of the foot keel with the medial being more anterior than the lateral to encourage fifth ray motion in gait as in the oblique low gear axis of rotation of the second to fifth metatarsals in the human foot.

The importance of biplanar motion capability can be appreciated when an amputee walks on uneven terrain or when the athlete cuts medially or laterally on the foot. The direction of the ground force vector changes from being sagittally oriented to having a frontal plane component. The ground will push medially in opposite direction to the foot pushing laterally. As a consequence to this, the calf shank leans medially and weight is applied to the medial structure of the foot keel. In response to these pressures, the medial expansion joint struts 25 and 31 of the foot keel 2 dorsiflex (deflect upward) and invert, and the lateral expansion joint struts 27 and 30 plantar flex (deflect downwards) and invert. This motion tries to put the plantar surface of the foot flat on the ground (plantar grade).

Figure 6:
FIG. 6 is a side view of another foot keel of the invention, especially for sprinting, which may be used in the prosthetic foot of the invention.
Figure 7:
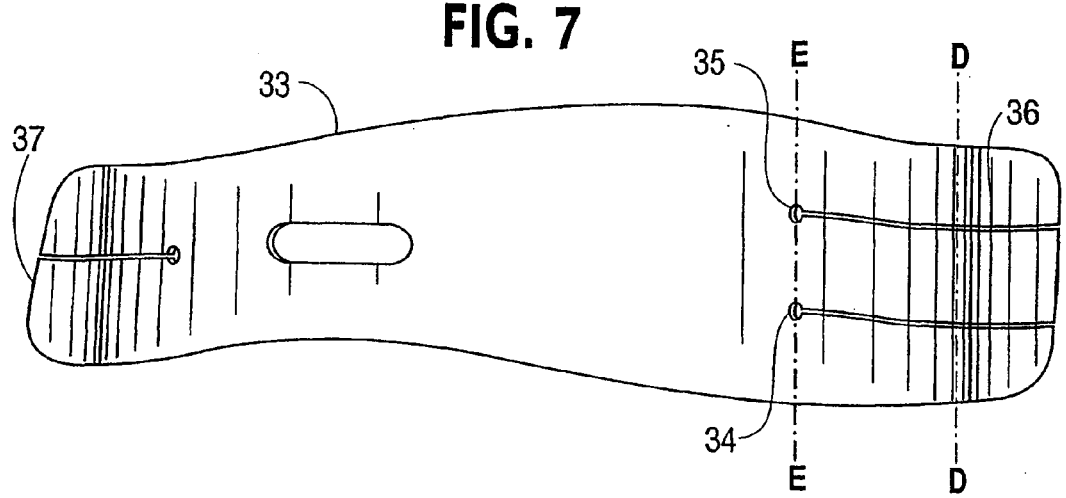
FIG. 7 is a top view of the foot keel of FIG. 6.

Another foot keel 33 of the invention, especially for sprinting, may be used in the prosthetic foot of the invention, see FIGS. 6 and 7. The body's center of gravity in a sprint becomes exclusively sagittal plane oriented. The prosthetic foot does not need to have a low dynamic response characteristic. As a consequence, the 15° to 35° external rotation orientation of the longitudinal axis of the forefoot, midfoot concavity as in foot keel 2 is not needed. Rather, the concavity's longitudinal axis D—D orientation should become parallel to the frontal plane as depicted in FIGS. 6 and 7. This makes the sprint foot respond in a sagittal direction only. Further, the orientation of the expansion joint holes 34 and 35 in the forefoot and midfoot portions, along line E—E, is parallel to the frontal plane, i.e., the lateral hole 35 is moved anteriorly and in line with the medial hole 34 and parallel to the frontal plane. The anterior terminal end 36 of the foot keel 33 is also made parallel to the frontal plane. The posterior terminal heel area 37 of the foot keel is also parallel to the frontal plane. These modifications effect in a negative way the multi-use capabilities of the prosthetic foot. However, its performance characteristics become task specific. Another variation in the sprint foot keel 33 is in the toe, ray region of the forefoot portion of the foot where 15° of dorsiflexion in the foot keel 2 are increased to 25–40° of dorsiflexion in foot keel 33.

Figure 9:
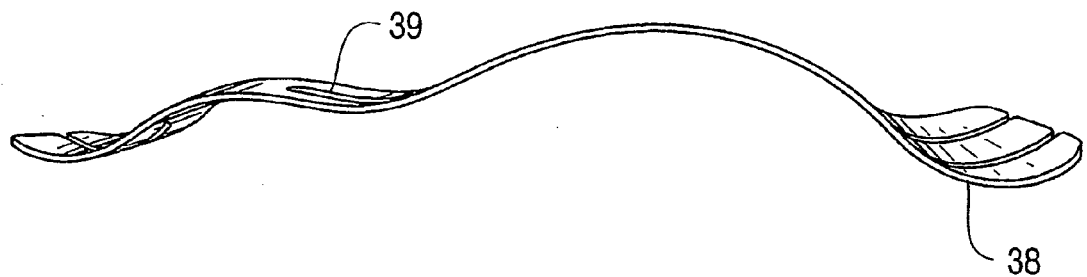
FIG. 9 is a side view of an additional foot keel of the invention for the prosthetic foot particularly useful for sprinting by an amputee that has had a Symes amputation of the foot.
Figure 10:
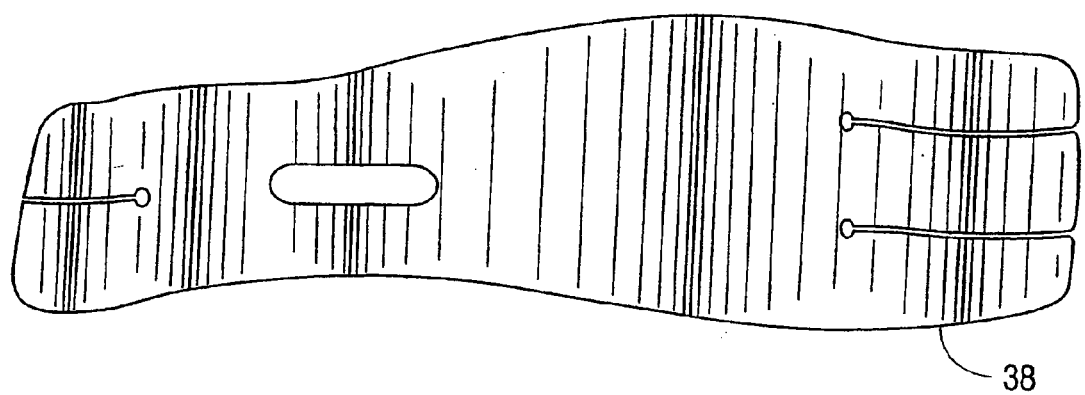
FIG. 10 is a top view of the foot keel of FIG. 9.
Figure 11:
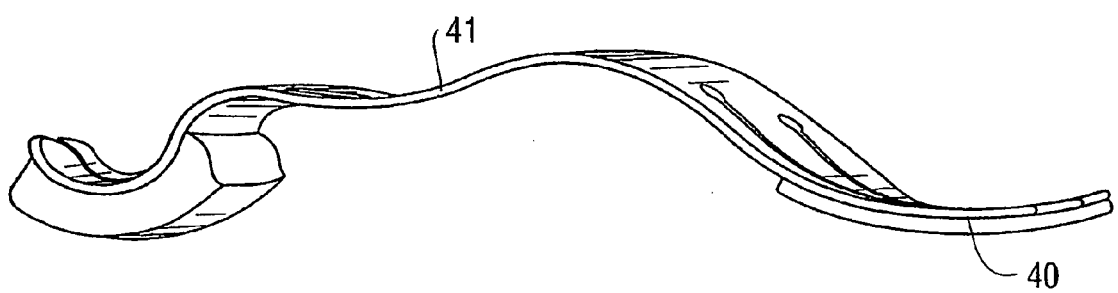
FIG. 11 is a further variation of foot keel for the prosthetic foot of the invention for a Symes amputee, the foot keel providing the prosthetic foot with high low dynamic response characteristics as well as biplanar motion capabilities.
Figure 12:
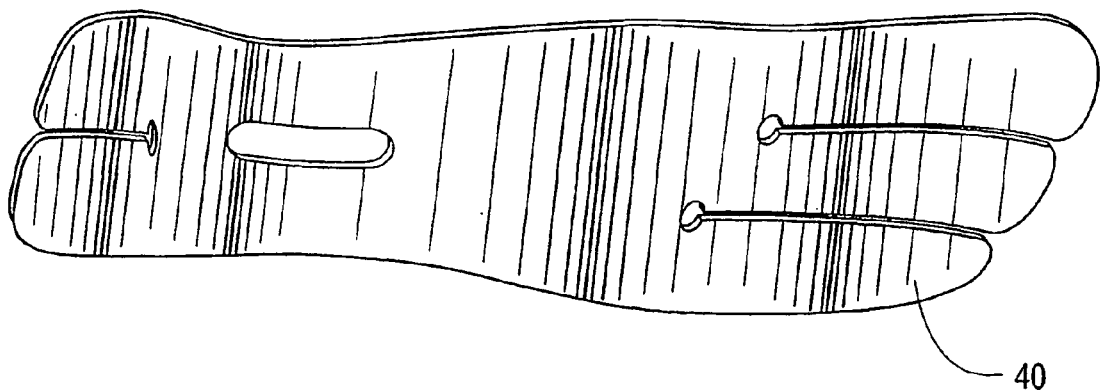
FIG. 12 is a top view of the foot keel of FIG. 11.

FIGS. 9 and 10 show an additional foot keel 38 of the invention for the prosthetic foot particularly useful for sprinting by an amputee that has had a Symes amputation of the foot. For this purpose, the midfoot portion of the foot keel 38 includes a posterior, upwardly facing concavity 39 in which the curved lower end of the calf shank is attached to the foot keel by way of the releasable fastener. This foot keel can be utilized by all lower extremity amputees. The foot keel 38 accommodates the longer residual limb associated with the Symes level amputee. Its performance characteristics are distinctively quicker in dynamic response capabilities. Its use is not specific to this level of amputation. It can be utilized on all transtibial and transfemoral amputations. The foot keel 40 in the example embodiment of FIGS. 11 and 12 also has a concavity 41 for a Symes amputee, the foot keel providing the prosthetic foot with high low dynamic response characteristic as well as biplanar motion capabilities like those of the example embodiment in FIGS. 3–5 and 8.

The functional characteristics of the several foot keels for the prosthetic foot 1 are associated with the shape and design features as they relate to concavities, convexities, radii size, expansion, compression, and material physical properties—all of these properties relating, to reacting to, ground forces in walking, running and jumping activities.

Figure 13:
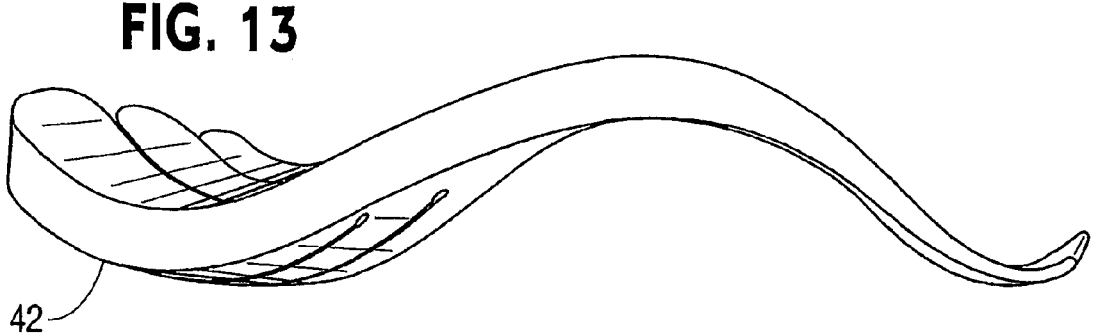
FIG. 13 is a side view of a foot keel of the invention wherein the thickness of the keel tapers, e.g., is progressively reduced, from the midfoot portion to the hindfoot portion of the keel.
Figure 14:
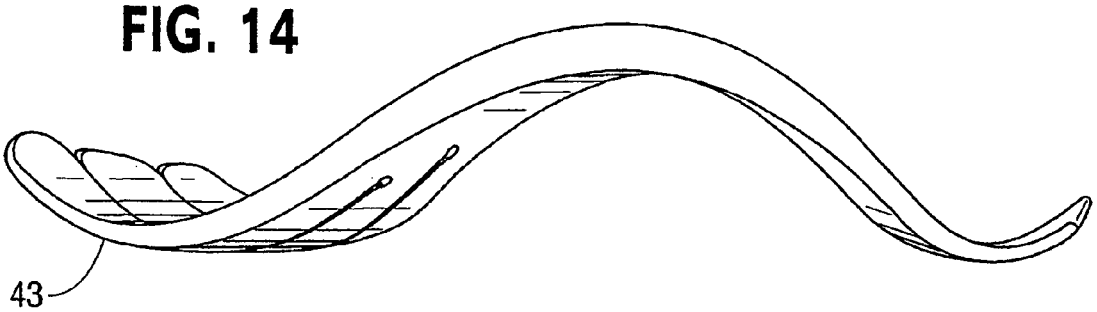
FIG. 14 is a side view of another form of the foot keel wherein the thickness tapers from the midfoot toward both the forefoot and hindfoot of the keel.
Figure 16:
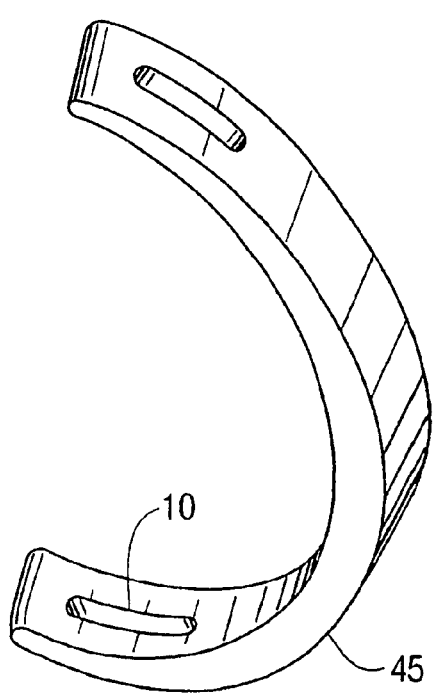
FIG. 16 is a side view like FIG. 15 but showing another calf shank tapered from the middle towards both its upper and lower ends.
Figure 17:
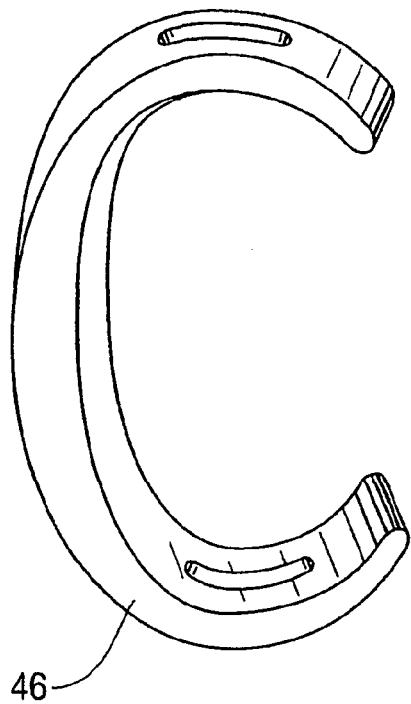
FIG. 17 is a side view of a C-shaped calf shank for the prosthetic foot, the calf shank thickness tapering from the middle towards both its upper and lower ends.
Figure 18:
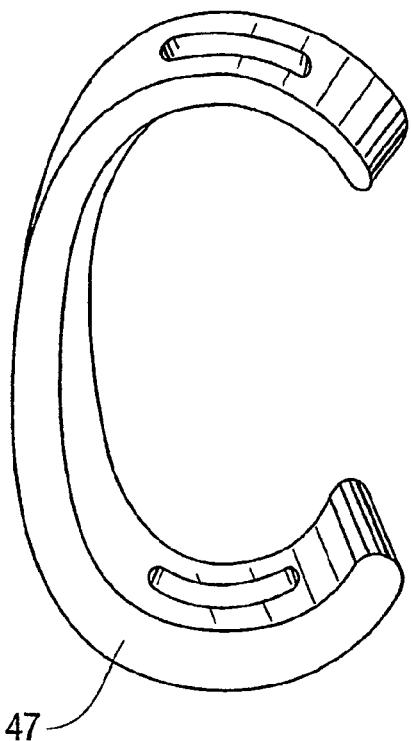
FIG. 18, is a side view of another example of a C-shaped calf shank for the prosthetic foot, the thickness of the calf shank being progressively reduced from its midportion to its upper end.
Figure 19:
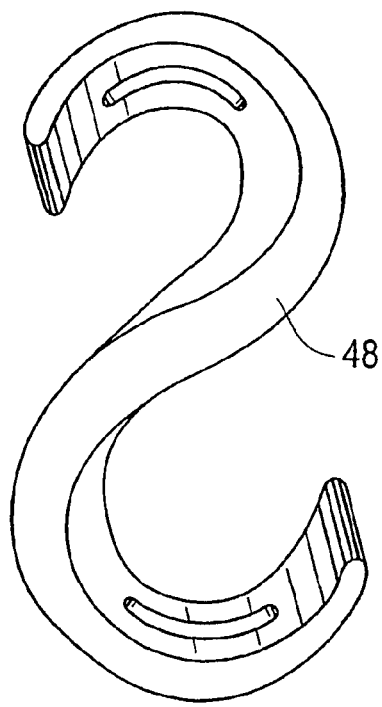
FIG. 19 is a side view of an S-shaped calf shank for the prosthetic foot, both ends being progressively reduced in thickness from the middle thereof.
Figure 20:
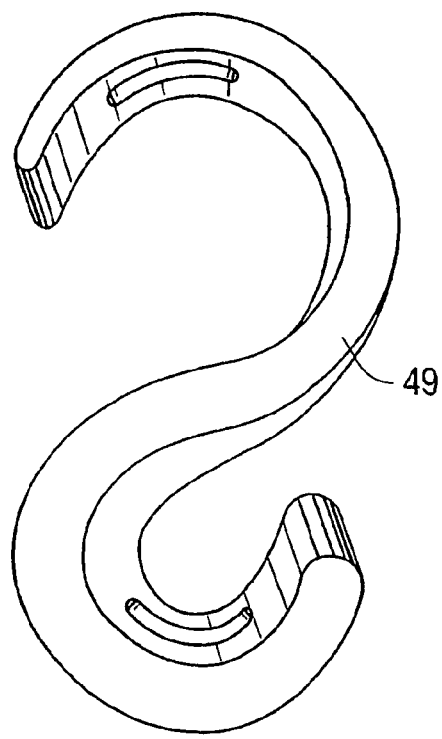
FIG. 20 is a further example of an S-shaped calf shank which is tapered in thickness only at its upper end.
Figure 21:
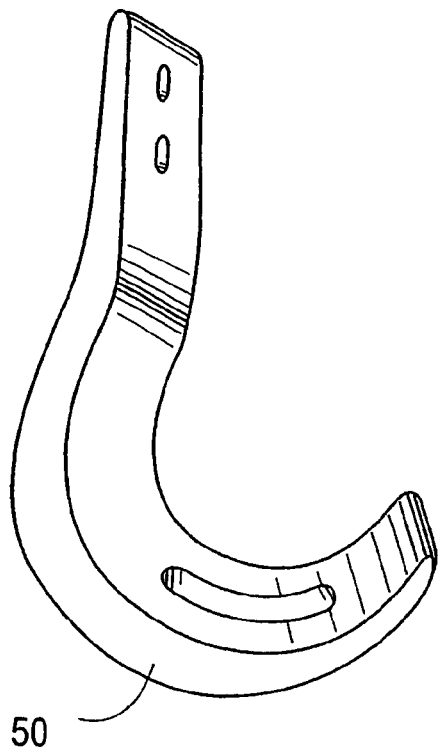
FIG. 21 is a side view of a J-shaped calf shank, tapered at each end, for the prosthetic foot of the invention.
Figure 22:
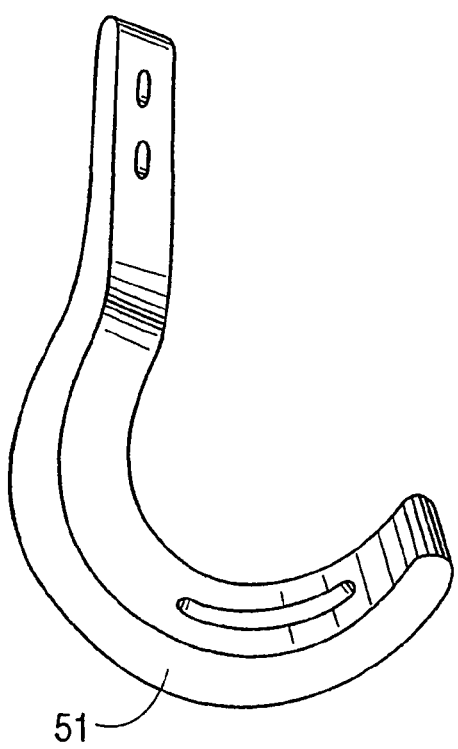
FIG. 22 is a view like FIG. 21 but showing a J-shaped calf shank which is progressively reduced in thickness towards only its upper end.

The foot keel 42 in FIG. 13 is like that in the example embodiment of FIGS. 3–5 and 8, except that the thickness of the foot keel is tapered from the midfoot portion to the posterior of the hindfoot. The foot keel 43 in FIG. 14 has its thickness progressively reduced or tapered at both its anterior and posterior ends. Similar variations in thickness are shown in the calf shank 44 of FIG. 14 and the calf shank 45 of FIG. 16 which may be used in the prosthetic foot 1. Each design of the foot keel and calf shank create different functional outcomes, as these function outcomes relate to the horizontal and vertical linear velocities which are specific to improving performance in varied athletic related tasks. The capability of multiple calf shank configurations and adjustments in settings between the foot keel and the calf shank create a prosthetic foot calf shank relationship that allows the amputee and/or the prosthetist the ability to tune the prosthetic foot for maximum performance in a selected one of a wide variety of sport and recreational activities.

Other calf shanks for the prosthetic foot 1 are illustrated in FIGS. 17–22 and include C-shaped calf shanks 46 and 47, S-shaped calf shanks 48 and 49 and J-shaped calf shanks 50 and 51. The upper end of the calf shank could also have a straight vertical end with a pyramid attachment plate attached to this proximal terminal end. A male pyramid could be bolted to and through this vertical end of the calf shank. Plastic or aluminum fillers to accept the proximal male pyramid and the distal foot keel could also be provided in the elongated openings at the proximal and distal ends of the calf shank. The prosthetic foot of the invention is a modular system preferably constructed with standardized units or dimensions for flexibility and variety in use.

All track related running activities take place in a counter-clockwise direction. Another, optional feature of the invention takes into account the forces acting on the foot advanced along such a curved path. Centripetal acceleration acts toward the center of rotation where an object moves along a curved path. Newton's third law is applied for energy action. There is an equal and opposite reaction. Thus, for every "center seeking" force, there is a "center fleeing" force. The centripetal force acts toward the center of rotation and the centrifugal force, the reaction force, acts away from the center of rotation. If an athlete is running around the curve on the track, the centripetal force pulls the runner toward the center of the curve while the centrifugal force pulls away from the center of the curve. To counteract the centrifugal force which tries to lean the runner outward, the runner leans inward. If the direction of rotation of the runner on the track is always counter-clockwise, then the left side is the inside of the track. As a consequence, according to a feature of the present invention, the left side of the right and left prosthetic foot calf shanks can be made thinner than the right side and the amputee runner's curve performance could be improved.

The foot keels 2, 33, 38, 42 and 43 in the several embodiments, are each 29 cm long with the proportions of the shoe 1 shown to scale in FIGS. 3, 4 and 5, and in the several views of the different calf shanks and foot keels. However, as will be readily understood by the skilled artisan, the specific dimensions of the prosthetic foot can be varied depending on the size, weight and other characteristics of the amputee being fitted with the foot.

The operation of the prosthetic foot 1 in walking and running stance phase gait cycles will now be considered. Newton's three laws of motion, that relate to law of inertia, acceleration and action-reaction, are the basis for movement kinematics in the foot 2. From Newton's third law, the law of action-reaction, it is known that the ground pushes on the foot in a direction equal and opposite to the direction the foot pushes on the ground. These are known as ground reaction forces. Many scientific studies have been done on human gait, running and jumping activities. Force plate studies show us that Newton's third law occurs in gait. From these studies, we know the direction the ground pushes on the foot.

The stance phase of walking/running activities can be further broken down into deceleration and acceleration phases. When the prosthetic foot touches the ground, the foot pushes anteriorly on the ground and the ground pushes back in an equal and opposite direction—that is to say the ground pushes posteriorly on the prosthetic foot. This force makes the prosthetic foot move. The stance phase analysis of walking and running activities begins with the contact point being the posterior lateral corner 18, FIGS. 3 and 18, which is offset more posteriorly and laterally than the medial side of the foot. This offset at initial contact causes the foot to evert and the calf shank to plantar flex. The calf shank always seeks a position that transfers the body weight through its shank, e.g., it tends to have its long vertical member in a position to oppose the ground forces. This is why it moves posteriorly—plantar flexes to oppose the ground reaction force which is pushing posteriorly on the foot. The ground forces cause the calf shank to compress with the proximal end moving posteriorly. The calf shank lower tight radius compresses simulating human ankle joint plantar flexion and the forefoot is lowered by compression to the ground. At the same time, the posterior aspect of the top of the foot keel 2 compresses upward through compression. Both of these compressive forces act as shock absorbers. This shock absorption is further enhanced by the offset posterior lateral heel 18 which causes the foot to evert, which also acts as a shock absorber, once the calf shank has stopped moving into plantar flexion and with the ground pushing posteriorly on the foot.

The compressed members of the foot keel and calf shank then start to unload—that is they seek their original shape and the stored energy is released—which causes the calf shank proximal end to move anteriorly in an accelerated manner. As the calf shank approaches its vertical starting position, the ground forces change from pushing posteriorly to pushing vertically upward against the foot. Since the prosthetic foot has posterior and anterior plantar surface weight bearing areas and these areas are connected by a non-weight bearing long arch shaped midportion, the vertically directed forces from the prosthesis cause the long arch shaped midportion to load by expansion. The posterior and anterior weight—bearing surfaces diverge. These vertically directed forces are being stored in the long arch midportion of the foot—as the ground forces move from being vertical in nature to anteriorly directed. The calf shank expands—simulating ankle dorsiflexion. This causes the prosthetic foot to pivot off of the anterior plantar weight-bearing surface. The hindfoot long arch changes from being compressed to being expanded. This releases the stored vertical compressed force energy into improved expansion capabilities.

The long arch of the foot keel and the calf shank resist expansion of their respective structures. As a consequence, the calf shank anterior progression is arrested and the foot starts to pivot off the anterior plantar surface weight—bearing area. The expansion of the midfoot portion of the foot keel has as high and low response capability in the case of the foot keels in the example embodiments of FIGS. 3–5 and 8, FIGS. 11 and 12, FIG. 13 and FIG. 14. Since the midfoot forefoot transitional area of these foot keels is deviated 25° to 35° externally from the long axis of the foot, the medial long arch is longer than the lateral long arch. This is important because in the normal foot, during acceleration or deceleration, the medial aspect of the foot is used.

The prosthetic foot longer medial arch has greater dynamic response characteristic than the lateral. The lateral shorter toe lever is utilized when walking or running at slower speeds. The body's center of gravity moves through space in a sinusoidal curve. It moves medial, lateral, proximal and distal. When walking or running at slower speeds, the body's center of gravity moves more medial and lateral than when walking or running fast. In addition, momentum or inertia is less and the ability to overcome a higher dynamic response capability is less. The prosthetic foot of the invention is adapted to accommodate these principles in applied mechanics.

As the ground forces push anteriorly on the prosthetic foot which is pushing posteriorly on the ground, as the heel begins to rise the anterior portion of the long arch of the midfoot portion is contoured to apply these posteriorly directed forces perpendicular to its plantar surface. This is the most effective and efficient way to apply these forces. The same can be said about the posterior hindfoot portion of the prosthetic foot. It is also shaped so that the posteriorly directed ground forces at initial contact are opposed with the foot keel's plantar surface being perpendicular to their applied force direction.

In the later stages of heel rise, toe off walking and running activities, the ray region of the forefoot portion is dorsiflexed 15°–35°. This upwardly extending arc allows the anteriorly directed ground forces to compress this region of the foot. This compression is less resisted than expansion and a smooth transition occurs to the swing phase of gait and running with the prosthetic foot. In later stages of stance phase of gait, the expanded calf shank and the expanded midfoot long arch release their stored energy adding to the propulsion of the amputee's body's center of gravity.

The posterior aspect of the hindfoot and the forefoot region of the foot keel incorporate expansion joint holes and expansion joint struts in several of the embodiments as noted previously. The orientation of the expansion joint holes act as a mitered hinge and biplanar motion capabilities are improved for improving the total contact characteristics of the plantar surface of the foot when walking on uneven terrain.

The Symes foot keels in FIGS. 9–12 are distinctively different in dynamic response capabilities—as these capabilities are associated with walking, running and jumping activities. These foot keels differ in four distinct features. These include the presence of a concavity in the proximate, posterior of the midfoot portion for accommodating the Symes distal residual limb shape better than a flat surface. The alignment concavity requires that the corresponding anterior and posterior radii of the arched foot keel midportion be more aggressive and smaller in size. As a consequence, all of the midfoot long arch radii and the hindfoot radii are tighter and smaller. This significantly affects the dynamic response characteristics. The smaller radii create less potential for a dynamic response. However, the prosthetic foot responds quicker to all of the aforementioned walking, running and jumping ground forces. The result is a quicker foot with less dynamic response.

Improved task specific athletic performance can be achieved with alignment changes using the prosthetic foot of the invention, as these alignment changes affect the vertical and horizontal components of each task. The human foot is a multi-functional unit—it walks, runs and jumps. The human tibia fibula calf shank structure on the other hand is not a multi-functional unit. It is a simple lever which applies its forces in walking, running and jumping activities parallel to its long proximal—distal orientation. It is a non-compressible structure and it has no potential to store energy. On the other hand, the prosthetic foot of the invention has dynamic response capabilities, as these dynamic response capabilities are associated with the horizontal and vertical linear velocity components of athletic walking, running and jumping activities and out-performing the human tibia and fibula. As a consequence, the possibility exists to improve amputee athletic performance. For this purpose, according to the present invention, the fastener 8 is loosened and the alignment of the calf shank and the foot keel with respect to one another is adjusted in the longitudinal direction of the foot keel. Such a change is shown in connection with FIGS. 1 and 2. The calf shank is then secured to the foot keel in the adjusted position with the fastener 8. During this adjustment, the bolt of the fastener 8 slides relative to one or both of the opposed, relatively longer, longitudinally extending openings 9 and 10 in the foot keel and calf shank, respectively.

An alignment change that improves the performance characteristic of a runner who makes initial contact with the ground with the foot flat as in sprinting, for example, is one wherein the foot keel is slid anterior relative to the calf shank and the foot plantar flexed on the calf shank. This new relationship improves the horizontal component of running. That is, with the calf shank plantar flexed to the foot, and the foot making contact with the ground in a foot flat position as opposed to initially heel contact, the ground immediately pushes posteriorly on the foot that is pushing anteriorly on the ground. This causes the calf shank to move rapidly forward (by expanding) and downwardly. Dynamic response forces are created by expansion which resists the calf shank's direction of initial movement. As a consequence, the foot pivots over the metatarsal plantar surface weight—bearing area. This causes the midfoot region of the keel to expand which is resisted more than compression. The net effect of the calf shank expansion and the midfoot expansion is that further anterior progression of the calf shank is resisted which allows the knee extenders and hip extenders in the user's body to move the body's center of gravity forward and proximal in a more efficient manner (i.e., improved horizontal velocity). In this case, more forward than up than in the case of a heel toe runner whose calf shank's forward progression is less resisted by the calf shank starting more dorsiflexed (vertical) than a foot flat runner.

To analyze the sprint foot in function, an alignment change of the calf shank and foot keel is made. Advantage is taken of the foot keel having all of its concavities with their longitudinal axis orientation parallel to the frontal plane. The calf shank is plantar flexed and slid posterior on the foot keel. This lowers the distal circles even further than on the flat foot runner with the multi-use foot keel like that in FIGS. 3–5 and 8, for example. As a consequence, there is even greater horizontal motion potential and the dynamic response is directed into this improved horizontal capability.

The sprinters have increased range of motion, forces and momentum (inertia)—momentum being a prime mover. Since their stance phase deceleration phase is shorter than their acceleration phase, increased horizontal linear velocities are achieved. This means that at initial contact, when the toe touches the ground, the ground pushes posteriorly on the foot and the foot pushes anteriorly on the ground. The calf shank which has increased forces and momentum is forced into even greater flexion and downward movement than the initial contact foot flat runner. As a consequence to these forces, the foot's long arch concavity is loaded by expansion and the calf shank is loaded by expansion. These expansion forces are resisted to a greater extent than all the other previously mentioned forces associated with running. As a consequence, the dynamic response capability of the foot is proportional to the force applied. The human tibia fibula calf shank response is only associated with the energy force potential—it is a straight structure and it cannot store energy. These expansion forces in the prosthetic foot of the invention in sprinting are greater in magnitude than all the other previously mentioned forces associated with walking and running. As a consequence, the dynamic response capability of the foot is proportional to the applied forces and increased amputee athletic performance, as compared with human body function, is possible.

Figure 25:
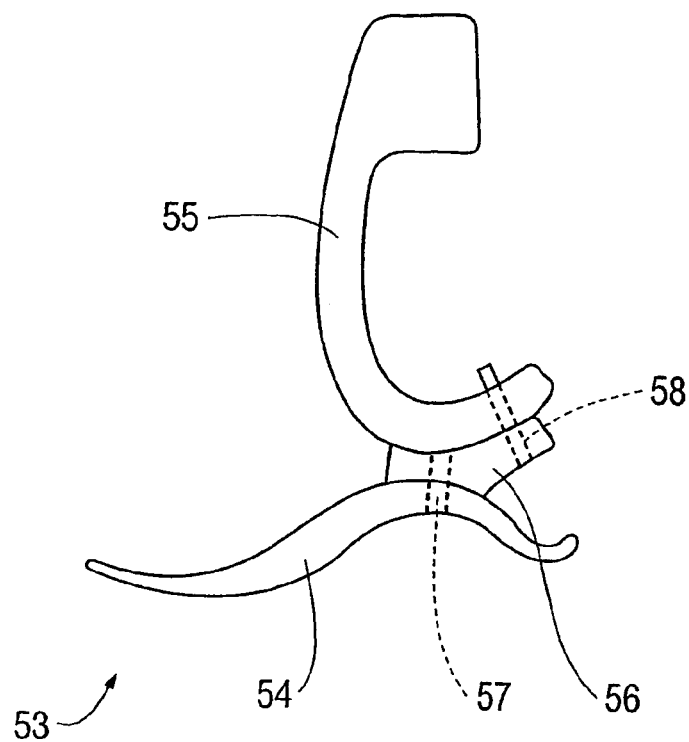
FIG. 25 is a side view of another prosthetic foot of the invention similar to that in FIG. 3, but showing use of a coupling element with two releasable fasteners spaced longitudinally connecting the element to the calf shank and foot keel, respectively.

The prosthetic foot 53 depicted in FIG. 25 is like that in FIG. 3 except for the adjustable fastening arrangement between the calf shank and the foot keel and the construction of the upper end of the calf shank for connection to the lower end of a pylon. In this example embodiment, the foot keel 54 is adjustably connected to the calf shank 55 by way of plastic or aluminum coupling element 56. The coupling element is attached to the foot keel and calf shank by respective releasable fasteners 57 and 58 which are spaced from one another in the coupling element in a direction along the longitudinal direction of the foot keel. The fastener 58 joining the coupling element to the calf shank is more posterior than the fastener 57 joining the foot keel and the coupling element. By increasing the active length of the calf shank in this way, the dynamic response capabilities of the calf shank itself are increased. Changes in alignment are made in cooperation with longitudinally extending openings in the calf shank and foot keel as in other example embodiments.

The upper end of the calf shank 55 is formed with an elongated opening 59 for receiving a pylon 15. Once received in the opening, the pylon can be securely clamped to the calf shank by tightening bolts 60 and 61 to draw the free side edges 62 and 63 of the calf shank along the opening together. This pylon connection can be readily adjusted by loosening the bolts, telescoping the pylon relative to the calf shank to the desired position and reclamping the pylon in the adjusted position by tightening the bolts.

Figure 26:
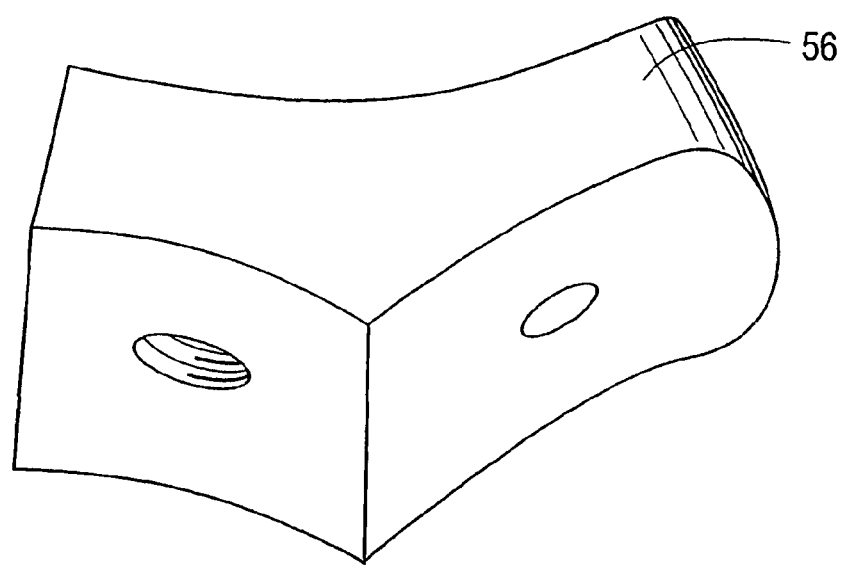
FIG. 26 is an enlarged side view of the coupling element in FIG. 25.
Figure 27:
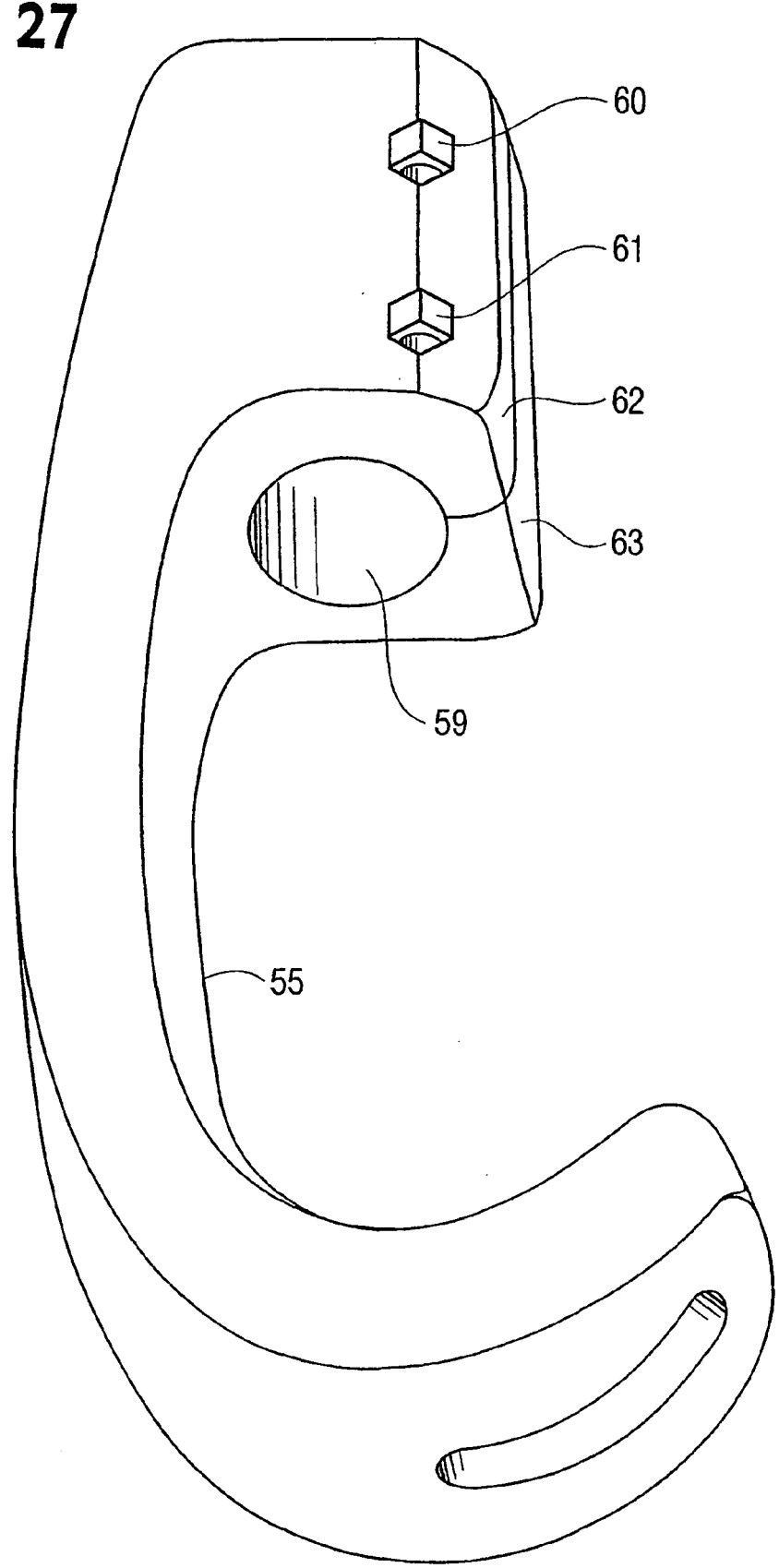
FIG. 27 is an enlarged side view of the calf shank of the prosthetic foot of FIG. 25.
Figure 28:
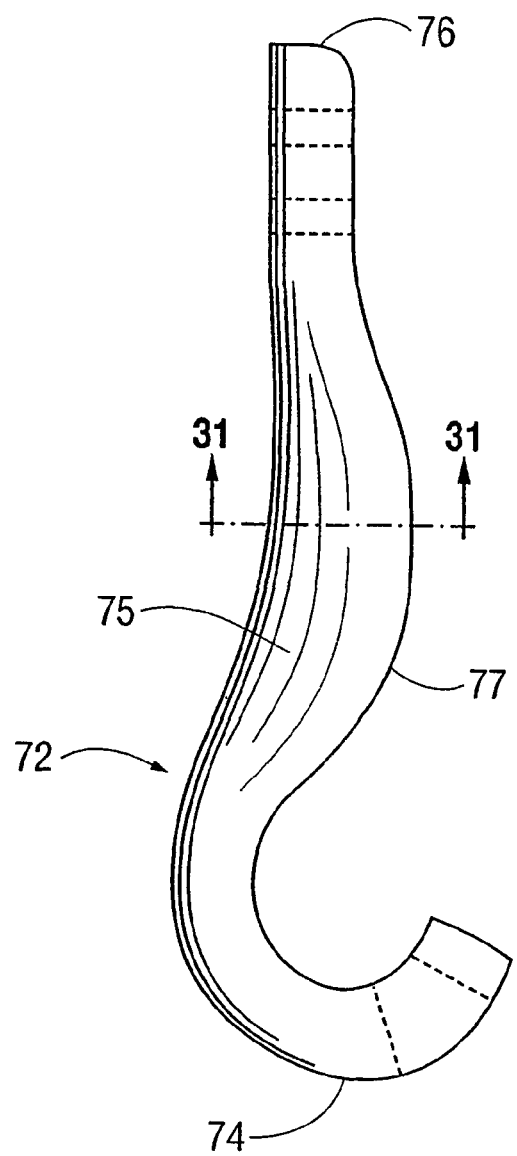
FIG. 28 is a side view of another calf shank of the prosthetic foot of the invention, having a reversely curved portion above the generally parabola shaped lower end.
Figure 31:
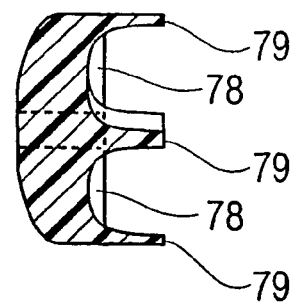
FIG. 31 is a sectional view of the calf shank of FIGS. 28–30 taken along the line 31—31 in FIG. 28.
Figure 29:
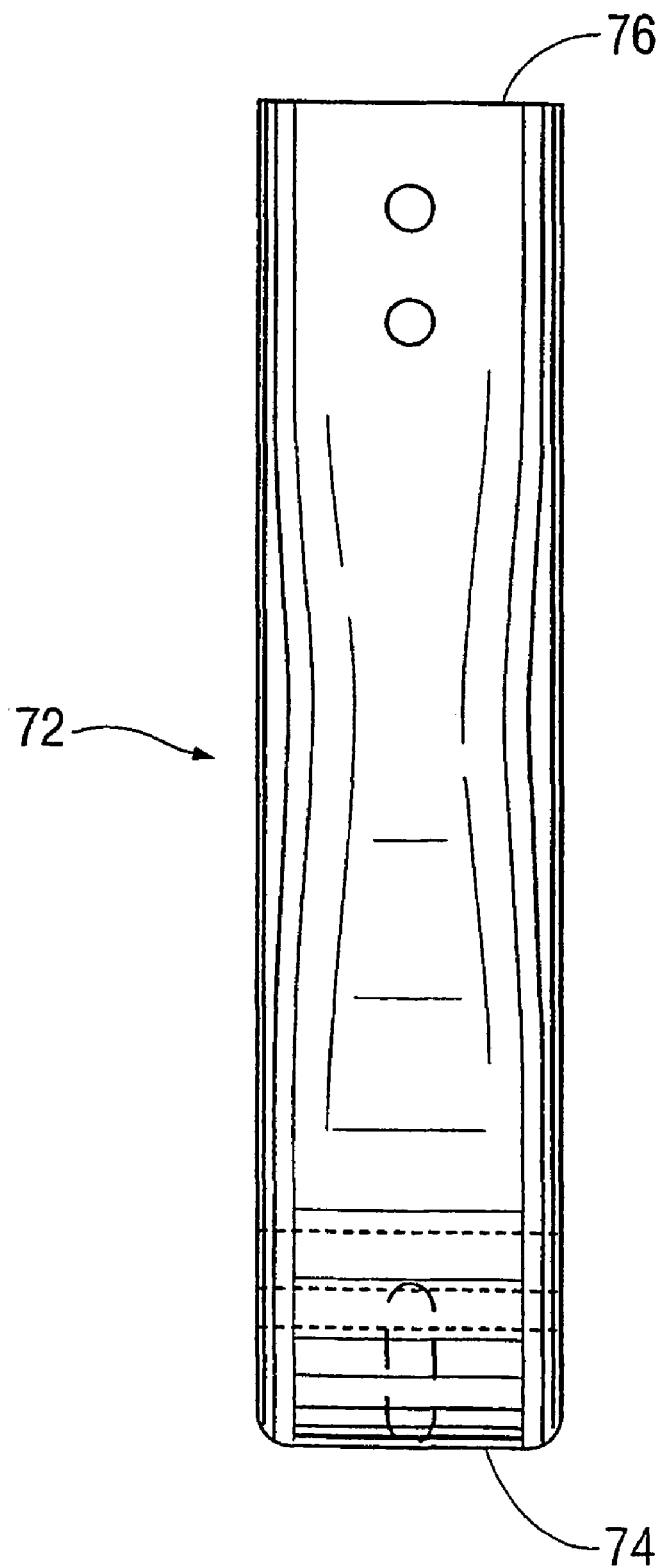
FIG. 29 is a left side view of the calf shank of FIG. 28.
Figure 30:
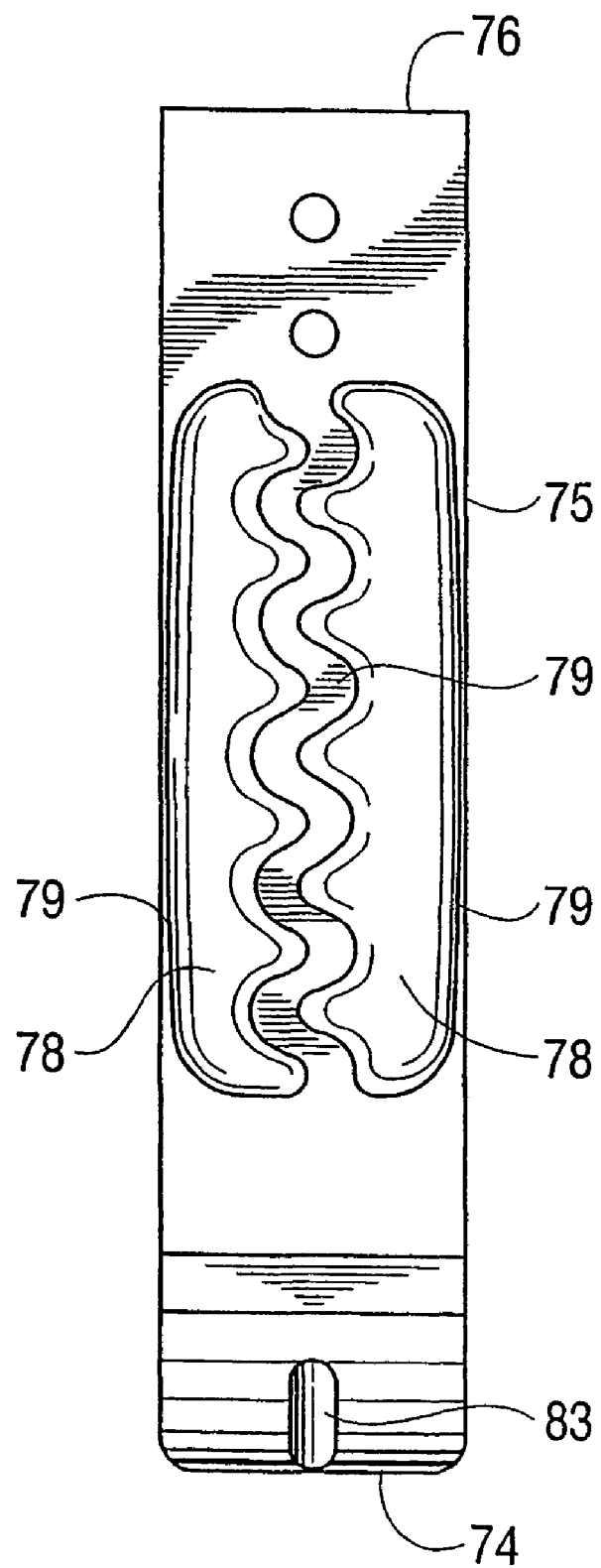
FIG. 30 is a right side view of the calf shank of FIG. 28 showing a plurality of S-shaped grooves and fins extending longitudinally on the posteriorly facing, reversely curved portion of the calf shank.
Figure 32:
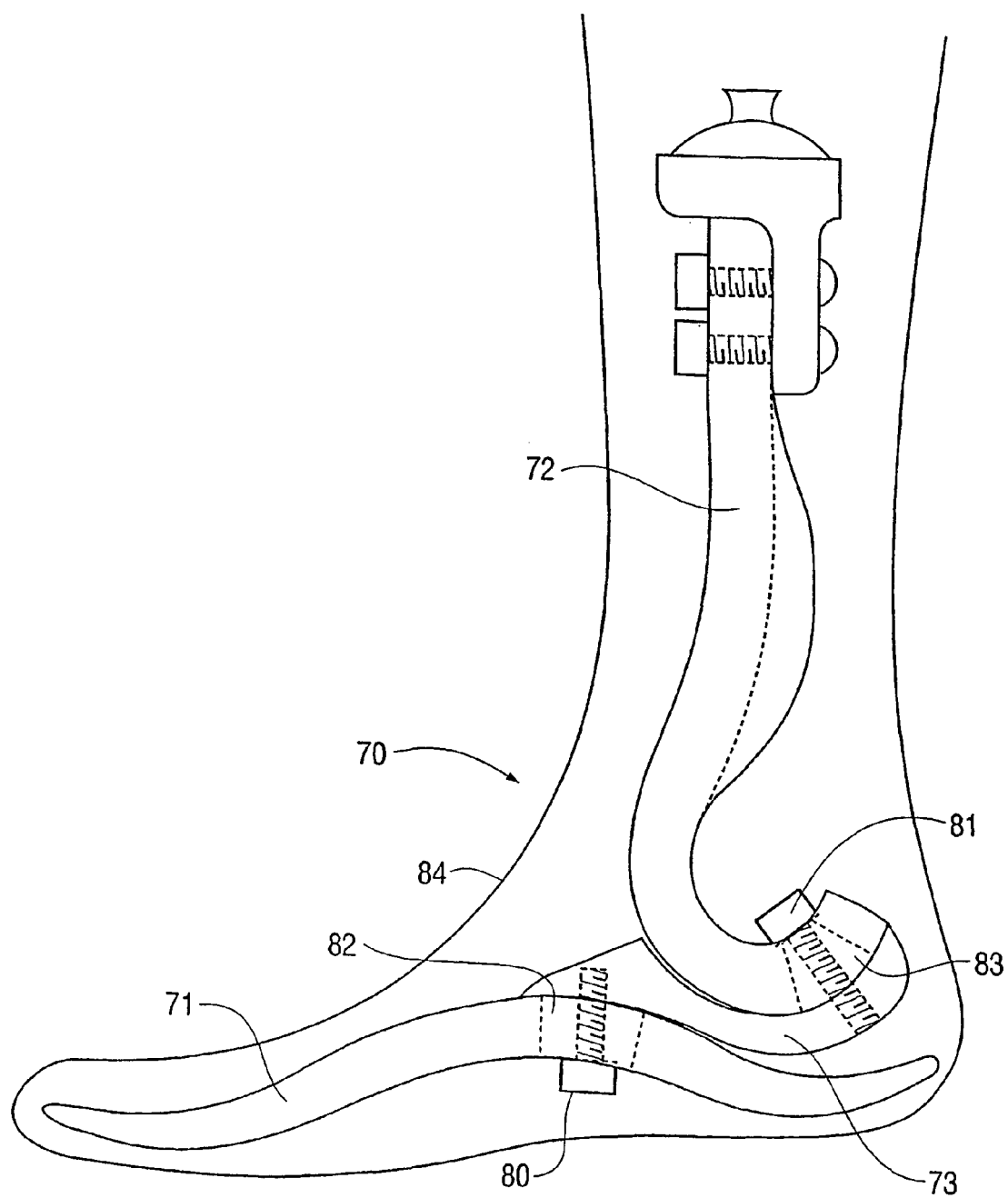
FIG. 32 is a. side view of another embodiment of the prosthetic foot of the invention wherein the calf shank of FIGS. 28–31 is utilized within a cosmetic covering of the foot.

The prosthetic foot 70 according to a further embodiment of the invention is depicted in FIG. 32. The prosthetic foot comprises a foot keel 71, a calf shank 72 and a coupling element 73. The prosthetic foot 70 is similar to the prosthetic foot 53 in the embodiment of FIGS. 25–27, except that the calf shank 72 in the prosthetic foot 70 is formed with a downward, convexly curved lower end 74 which extends upwardly, and initially anteriorly on the foot keel 71 into a reversely curved portion 75 of the calf shank leading to an upstanding upper end 76 thereof As shown in more detail in FIGS. 28–31, the calf shank 72 is generally parabola shaped at its lower end with the smallest radius of curvature thereof located at the lower end.

The reversely curved portion 75 of the calf shank has a posteriorly facing surface 77 which is provided with a plurality of longitudinally extending grooves 78 and fins 79 thereon. The fins and grooves facilitate resilient compression of the calf shank while resisting expansion thereof in response to forces on the calf shank during use of the prosthetic foot. In the example embodiment, the longitudinally extending grooves and fins are S-shaped, but could have other configurations, for example the grooves and fins could be linear. As in the previous embodiments, releasable fasteners 80 and 81 and longitudinally extending openings 82 and 83 in the calf shank and foot keel permit adjustment of the relationship of the respective, convexly curved surfaces of the foot keel and calf shank to tune the performance of the prosthetic foot. These convexly curved surfaces include a dorsal surface of a midfoot portion of the foot keel and the downward, convexly curved and anteriorly facing surface of the calf shank as in the previous embodiment. The relationship of these curves and the performance of the prosthetic foot have been explained with reference to FIGS. 1 and 2 of the drawings and related discussion above. The calf shank 72 and prosthetic foot 70 lend themselves to the use with a cosmetic covering 84 in the shape of a human foot and lower leg as shown in FIG. 32. The cosmetic covering is located over the foot keel and at least the lower end of the calf shank with the calf shank rising upwardly from the foot keel within the lower leg covering.

This concludes the description of the example embodiments. Although the present invention has been described with reference to a number of illustrative embodiments, it should be understood that numerous other modifications and embodiments can be devised by those skilled in the art that will fall within the spirit and scope of the principles of this invention. More particularly, reasonable variations and modifications are possible in the component parts and/or arrangements of the subject combination arrangement within the scope of the foregoing disclosure, the drawings, and the appended claims without departing from the spirit of the invention. For example, the several features of the invention in the various embodiments can be used together or substituted one for the other. The coupling element of the prosthetic foot could also be made of a resilient material, such as of carbon fiber and a high strength polyurethane material, and shaped to impart subtalar joint functional motion outcome potential. Further, the components of calf shank, coupling element and foot keel could be integrally formed as a one piece (non-adjustable) prosthetic foot for low cost, or as a two piece prosthetic foot providing at least some adjustability, according to the invention. In addition to variations and modifications in the component parts and/or arrangements, alternative uses will also be apparent to those skilled in the art.

What is claimed is:

1. A prosthetic foot comprising:
    a longitudinally extending foot keel;
    a calf shank secured to the foot keel at a lower end thereof and extending upwardly from the foot keel;
    wherein the lower end of the calf shank is downward, convexly curved and extends upwardly, and initially anteriorly therefrom into a reversely curved portion of the calf shank leading to an upstanding upper end thereof;
    wherein the reversely curved portion of the calf shank has a posteriorally facing surface which is provided with a plurality of S-shaped longitudinally extending grooves and fins formed thereon to facilitate resilient compression thereof in response to forces on the calf shank during use of the prosthetic foot.

2. The prosthetic foot according to claim 1, wherein the lower end of the calf shank is generally parabola shaped with the smallest radius of curvature thereof located at the lower end.

3. The prosthetic foot according to claim 1, wherein the calf shank extends upwardly from the foot keel above a hindfoot portion and the posterior part of a midfoot portion of the foot keel.

4. The prosthetic foot according to claim 1, further comprising a cosmetic covering in the shape of a human foot and lower leg, the cosmetic cover being located over the foot keel and at least the lower end of the calf shank with the calf shank rising upwardly from the foot keel within the lower leg covering.

5. The prosthetic foot according to claim 1, further comprising an adjustable fastening arrangement securing the calf shank to the foot keel, the fastening arrangement permitting adjustment of the relationship of the foot keel and calf shank to tune the performance of the prosthetic foot.

6. The prosthetic foot according to claim 5, wherein the adjustable fastening arrangement includes at least one releasable fastener and a longitudinally extending opening in the foot keel through which the fastener extends to permit adjustment of the alignment of the calf shank and foot keel in the longitudinal direction of the foot keel.

7. The prosthetic foot according to claim 1, wherein the calf shank is secured to the foot keel by way of a coupling element.

8. The prosthetic foot according to claim 1, wherein the calf shank and foot keel have respective convexly curved surfaces whose radii and relationship affect a dynamic response capability and motion outcome of the prosthetic foot in gait, the respective convexly curved surfaces including a dorsal surface of a midfoot portion of the foot keel and the downward, convexly curved and anteriorly facing surface of the calf shank.

9. The prosthetic foot according to claim 1, wherein the convexly curved lower end of the calf shank has a radius of curvature which increases as the calf shank extends upwardly from its curved lower end.

10. A prosthetic foot comprising:
    a longitudinally extending foot keel having a forefoot portion at one end, a hindfoot Portion at an opposite end and an upwardly arched midfoot portion extending between the forefoot and hindfoot portions;
    a coupling element connected to the upwardly arched midfoot portion of the foot keel by a first releasable fastener, the coupling element extending posteriorly in the longitudinal direction of the foot keel to where the coupling element is spaced above the hindfoot portion of the foot keel;
    a resilient, upstanding calf shank having a lower end connected to the foot keel by way of the coupling element to form an ankle joint area of the foot, and an upper end to connect with a supporting structure on an amputee's leg, the lower end of the calf shank being connected to the coupling element by a second releasable fastener spaced posteriorly in the longitudinal direction of the foot keel from the first releasable fastener for increasing the active length and dynamic response capability of the calf shank;
    wherein the lower end of the calf shank is downward, convexly curved and extends upwardly, and initially anteriorly therefrom into a reversely curved portion of the calf shank leading to the upper end thereof.

11. The prosthetic foot according to claim 10, further comprising an adjustable fastening arrangement to permit adjustment of the alignment of the calf shank and the foot keel with respect to one another in the longitudinal direction of the foot keel for tuning the performance of the prosthetic foot.

12. The prosthetic foot according to claim 11, wherein the adjustable fastening arrangement includes a longitudinally extending opening in the foot keel through which the first releasable fastener extends to permit said adjustment of the alignment of the foot keel and calf shank.

13. The prosthetic foot according to claim 10, wherein the convexly curved lower end of the calf shank has a radius of curvature which increases as the calf shank extends upwardly from its curved lower end.

14. The prosthetic foot according to claim 10, wherein the lower end of the calf shank is generally parabola shaped with the smallest radius of curvature thereof located at the lower end.

15. The prosthetic foot according to claim 10, further comprising a cosmetic covering in the shape of a human foot and lower leg, the cosmetic covering being located over the foot keel and at least the lower end of the calf shank with the calf shank rising upwardly from the foot keel within the lower leg covering.

16. A prosthetic foot comprising:
- a longitudinally extending foot keel;
- a coupling element connected to the foot keel;
- a resilient, upstanding calf shank having a lower end connected to the foot keel by way of the coupling element to form an ankle joint area of the foot, and an upper end to connect with a supporting structure on an amputee's leg;
- wherein the lower end of the calf shank is downward, convexly curved and extends upwardly, and initially anteriorly therefrom into a reversely curved portion of the calf shank leading to the upper end thereof;
- wherein the reversely curved portion of the calf shank has a posteriorly facing surface which is provided with a plurality of S-shaped longitudinally extending grooves and fins formed thereon to facilitate resilient compression of the calf shank while resisting expansion thereof in response to forces on the calf shank during use of the prosthetic foot.

17. A calf shank for a prosthetic foot comprising:
- an elongated, semi-rigid resilient member having an outward convexly curved portion at one end of said member for attachment to a foot keel to form an ankle area of the prosthetic foot, an opposite end of said member to connect with a supporting structure on an amputee's leg, and wherein said convexly curved portion at said one end of said member extends from the one end and into a reversely curved portion of the calf shank leading to the opposite end;
- wherein the reversely curved portion of the calf shank has a conversely curved face with a plurality of S-shaped longitudinally extending grooves and fins formed thereon to facilitate resilient compression of the calf shank while resisting expansion thereof in response to forces on the calf shank during use of the calf shank in a prosthetic foot.

18. The calf shank according to claim 17, further comprising a fastening arrangement including a longitudinally extending opening in said convexly curved one end of said member along which a fastener for connecting said calf shank to a foot keel can be slid.

19. The calf shank according to claim 17, wherein the convexly curved one end has a generally parabola shape with the smallest radius of the curvature located at the one end.

20. The calf shank according to claim 17, wherein the convexly curved one end has a radius of curvature which increases as the calf shank extends from the one end.

\* \* \* \* \*